United States Patent [19]

Naito et al.

[11] Patent Number: 4,507,380

[45] Date of Patent: * Mar. 26, 1985

[54] HEAT-DEVELOPABLE COLOR PHOTOGRAPHIC MATERIAL CONTAINING DYE RELEASING COUPLERS

[75] Inventors: Hideki Naito; Hiroshi Hara; Kozo Sato; Yoshiharu Yabuki, all of Kanagawa, Japan

[73] Assignee: Fuji Photo Film Co., Ltd., Kanagawa, Japan

[*] Notice: The portion of the term of this patent subsequent to Oct. 2, 2001 has been disclaimed.

[21] Appl. No.: 389,341

[22] Filed: Jun. 17, 1982

[30] Foreign Application Priority Data

Jun. 17, 1981 [JP] Japan ................................ 56/93533

[51] Int. Cl.$^3$ .......................... G03C 5/54; G03C 1/40
[52] U.S. Cl. .................................... 430/203; 430/213; 430/226; 430/351; 430/543; 430/545; 430/619
[58] Field of Search ............... 430/203, 213, 226, 351, 430/619, 543, 545, 617, 618

[56] References Cited

U.S. PATENT DOCUMENTS

| | | | |
|---|---|---|---|
| 3,531,286 | 9/1970 | Renfrew | 430/351 |
| 3,761,270 | 9/1973 | de Mauriac et al. | 430/351 |
| 4,021,240 | 5/1977 | Cerquone et al. | 430/203 |
| 4,022,617 | 5/1977 | McGuckin | 430/203 |

OTHER PUBLICATIONS

Kokit, "Positive Images...Materials", *Research Disclosure*, No. 16408, 12/1977, pp. 15 & 16.

*Primary Examiner*—Richard L. Schilling
*Attorney, Agent, or Firm*—Sughrue, Mion, Zinn, Macpeak and Seas

[57] ABSTRACT

A heat-developable color photographic material is disclosed. The material is comprised of a support having thereon a layer containing at least a photographic silver halide and the photographic material containing an organic silver salt oxidizing agent, a reducing agent, a[hydrophobic]binder and a dye releasing compound which releases a diffusible dye upon heat development. The material is characterized by a support capable of receiving a released dye or a support having thereon a layer composed of an organic high molecular weight compound which is capable of receiving a released dye. The heat-developable color photographic material can easily provide a clear and stable color image by imagewise exposure to light and a heat development procedure. A process for forming a color image using the heat-developable color photographic material is also disclosed.

33 Claims, No Drawings

HEAT-DEVELOPABLE COLOR PHOTOGRAPHIC MATERIAL CONTAINING DYE RELEASING COUPLERS

FIELD OF THE INVENTION

The present invention relates to a process of forming a color image by heat development. Particularly, the present invention relates to a novel process for obtaining a color image by heat diffusion transfer of a dye released upon heat development of a heat developable color photographic material containing a dye releasing compound which releases a diffusible dye upon heat development into a support which is capable of receiving the released dye.

BACKGROUND OF THE INVENTION

Photographic processes using silver halide have been most widely used in the past due to their excellent photographic properties such as sensitivity or control of gradation, etc., as compared with other photographic processes, such as, an electrophotographic process or a diazo photographic process. In recent years, with respect to image formation processes for photographic materials using silver halide, many techniques capable of obtaining images with ease and rapidly have been developed by changing the conventional wet process using a developing solution into a dye process such as a process using heat, etc.

Heat-developable photographic materials are known in the field of these techniques, and heat-developable photographic materials and processes therefor have been described in U.S. Pat. Nos. 3,152,904, 3,301,678, 3,392,020 and 3,457,075, British Pat. Nos. 1,131,108 and 1,167,777, and *Research Disclosure*, No. 17029, pages 9 to 15 (June, 1978).

Many different processes for obtaining color images have been proposed. With respect to processes for forming color images by the reaction of an oxidation product of a developing agent with a coupler, it has been proposed to use a p-phenylenediamine type reducing agent and a phenolic coupler or an active methylene coupler as described in U.S. Pat. No. 3,531,286, a p-aminophenol type reducing agent as described in U.S. Pat. No. 3,761,270, a sulfonamidophenol type reducing agent as described in Belgian Pat. No. 802,519 and *Research Disclosure*, pages 31 and 32, (September, 1975) and the combination of a sulfonamidophenol type reducing agent and a 4-equivalent coupler as described in U.S. Pat. No. 4,021,240. These processes, however, are disadvantageous in that turbid color images are formed, because a reduced silver image and a color image are simultaneously formed on the exposed area after heat development. In order to eliminate these disadvantages, there have been proposed a process which comprises removing a silver image by liquid processing or a process which comprises transferring only the dye to another layer, for example, a sheet having an image receiving layer. However, the latter process is not desirable because it is not easy to transfer only the dye as distinguishable from unreacted substances.

Another process which comprises introducing a nitrogen containing heterocyclic group into a dye, forming a silver salt and releasing a dye by heat development has been described in *Research Disclosure*, No. 16966, pages 54 to 58 (May, 1978). According to this process, clear images cannot be obtained, because it is difficult to control the release of dyes from nonexposed areas, and thus it is not a conventional process.

Also, processes for forming a positive color image by a thermal silver dye bleach process, with useful dyes and methods for bleaching have been described, for example, in *Research Disclosure*, No. 14433, pages 30 to 32 (April, 1976), ibid., No. 15227, pages 14 and 15 (December, 1976) and U.S. Pat. No. 4,235,957.

However, this process requires an additional step and an additional material for accelerating bleaching of dyes, for example, heating with a superposed activating agent sheet. Furthermore, it has a drawback that the resulting color images are gradually reduced and bleached by coexisting free silver during preservation for a long period of time.

Moreover, a process for forming a color image utilizing a leuco dye has been described, for example, in U.S. Pat. Nos. 3,985,565 and 4,022,617. However, this process is not desirable because it is difficult to stably incorporate the leuco dye in the photographic material and coloration gradually occurs during preservation.

It is also known in the field of textiles to dye polyester with an azo dye. Although processes for application of the dyeing of polyester to a photographic field have been proposed, sufficiently desirable results have not been obtained. For example, a process for using a polyester film as an image recieving layer is described in U.S. Pat. No. 4,235,957. However, according to this process, the diffusion of dyes to a polyester film and the bleaching of dyes occurs simultaneously in order to form a positive image by a silver dye bleach process, and thus it is difficult to form an image with a good S/N value.

A process for transferring a dye formed upon the coupling reaction of a hydrazone developing agent with a coupler into a polyester support is described, for example, in British Pat. No. 2,056,103. However, this process does not provide a sufficient image since a dye forming efficiency of the coupling reaction is low and the transferring property to the support is poor.

SUMMARY OF THE INVENTION

The present invention provides a novel process for forming a color image using a heat-developable color photographic material eliminating the drawbacks of known materials.

Therefore, an object of the present invention is to provide a novel process for forming a color image which comprises directly transferring a diffusible dye into a support capable of receiving the dye, in contrast with a conventional method in which the diffusible dye is transferred into an image receiving layer containing a mordant.

Another object of the present invention is to provide a process for obtaining a clear color image using a photographic material having a simple composition.

Still another object of the present invention is to provide a process for obtaining a color image which is stable for a long period of time.

These and other objects of the present invention will become more apparent from the following detailed description and examples.

These objects of the present invention are attained by a heat-developable color photographic material comprising a support having thereon a layer containing at least a photographic silver halide and the photographic material containing an organic silver salt oxidizing agent, a reducing agent, a binder and a dye releasing compound which releases a diffusible dye upon heat development and the support being capable of receiving a released dye or the support having thereon a layer composed of an organic high molecular weight compound which is capable of receiving a released dye.

DETAILED DESCRIPTION OF THE INVENTION

The heat-developable color photographic material of the present invention can simultaneously provide a silver image having a negative-positive relationship to the original and a diffusible dye on the part corresponding to the silver image by only carrying out heat development after imagewise exposure to light. That is, when the heat-developable color photographic material of the present invention is imagewise exposed to light and developed by heating at a temperature range from 80° C. to 200° C., the oxidation-reduction reaction occurs between the organic silver salt oxidizing agent and the reducing agent by means of exposed photographic silver halide as a catalyst to form a silver image in the exposed area. In this step, the oxidized product of the reducing agent causes a coupling reaction with the dye releasing compound and as a result a diffusible dye is released. The diffusible dye thus released diffuses into a support which is capable of receiving a dye through a binder. In consequence, a negative dye image is formed in the support.

According to this process, an unreacted dye releasing compound hardly diffuses into the support mainly because the molecule is bulky. Furthermore, the reducing agent, oxidized product thereof and a coupling product hardly diffuses into the support mainly because their molecules are bulky, but also due to their difference in affinity with the support. In addition, only the released dye diffuses into the support. Therefore, a very clear image can be obtained which is an advantage of the present invention. Further, since a dye is previously incorporated into a dye releasing compound in this process, the conditions for the coupling reaction or bleaching during heat development are not required. Accordingly, any dye which is readily diffusible into the support may be used, which is another advantage of the present invention. According to the process, most of the diffusible dyes released can be diffusion-transferred into a support by an appropriate selection of a dye, a binder and a support. Accordingly, the image forming efficiency of the present invention is surprisingly high in dry processes.

The dye releasing compound which releases a diffusible dye which can be used in the present invention is represented by the following general formula:

C—L—D wherein C represents a substratum capable of bonding to an oxidized product which is formed by a reaction between a reducing agent and an organic silver salt oxidizing agent; D represents a dye portion for forming an image; and L represents a connecting group between C and D and the bond between C and L is cleaved upon the reaction of C with the oxidized product of the reducing agent.

The substratum represented by C is capable of bonding to an oxidized product which is formed by a reaction between a reducing agent and an organic silver salt oxidizing agent and includes an active methylene residue, an active methine residue, a phenol residue, a naphthol residue, etc. Preferred examples of the substrata are represented by the following general formulae (I) to (VII)

(I)

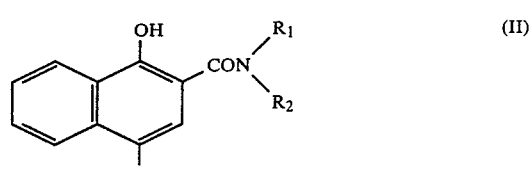

(II)

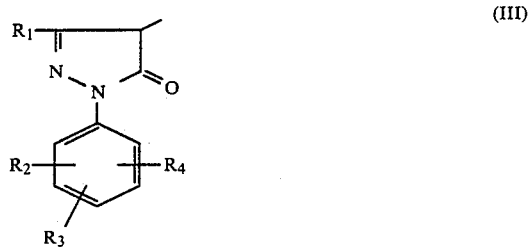

(III)

(IV)

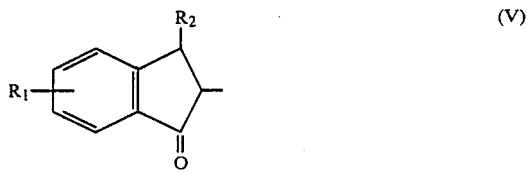

(V)

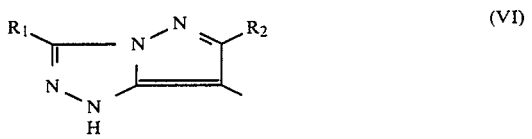

(VI)

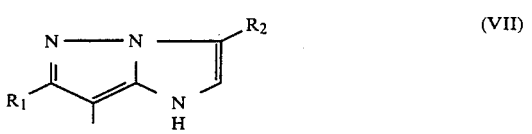

(VII)

wherein $R_1$, $R_2$, $R_3$ and $R_4$, which may be the same or different, each represents a hydrogen atom or a substituent selected from the group consisting of an alkyl group, a cycloalkyl group, an aryl group, an alkoxy group, an aryloxy group, an aralkyl group, an acyl group, an acylamino group, an alkoxyalkyl group, an aryloxyalkyl group, an N-substituted carbamoyl group, an alkylamino group, an arylamino group, a halogen atom, an acyloxy group and a cyano group, and these substituents may be further substituted with a hydroxyl group, a carboxyl group, a sulfo group, a cyano group, a nitro group, a sulfamoyl group, an N-substituted sulfamoyl group, a carbamoyl group, an N-substituted carbamoyl group, an acylamino group, an alkylsulfonylamino group, an arylsulfonylamino group, an alkyl group, an aryl group, an alkoxy group, an aryloxy group, an aralkyl group or an acyl group.

The substratum represented by C has preferably 12 to 40 carbon atoms and functions by releasing a diffusible dye when bonding to an oxidized product of the reducing agent and should contain a ballast group in order to prevent coloring of the support capable of receiving a dye with the dye releasing compound per se while heating. Examples of the ballast groups include a hydrophobic group, for example, an alkyl group, an alkoxyalkyl group, an aryloxyalkyl group, etc., and a hydrophilic group, for example, a carboxy group or a salt thereof, a sulfo group or a salt thereof, a phosphoric acid group or a salt thereof, a carbonamido group, a sulfonamido group, etc. It is preferred that the total number of the carbon atoms contained in the ballast group is 6 or more and that the total number of the carbon atoms contained in the substratum of C is 12 or more.

Specific examples of preferred substrata represented by C are set forth below, but the present invention is not to be construed as being limited thereto.

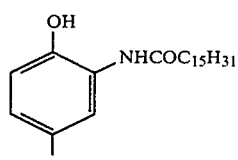
(C-1)

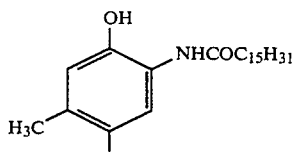
(C-2)

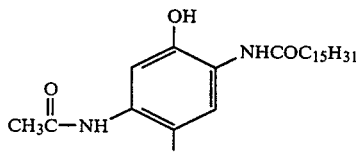
(C-3)

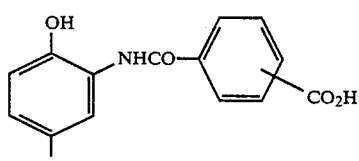
(C-4)

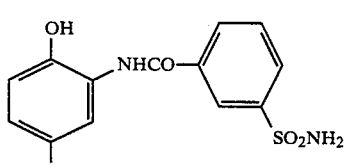
(C-5)

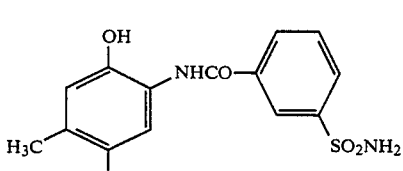
(C-6)

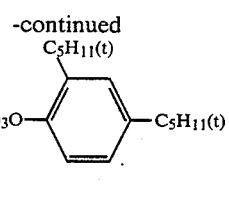
(C-7)

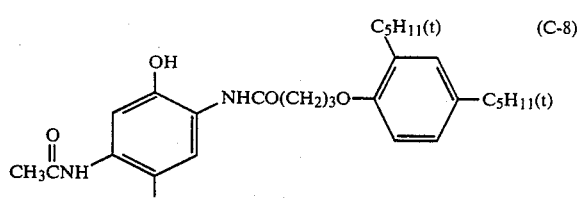
(C-8)

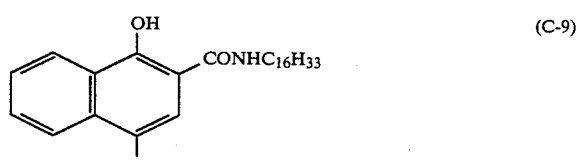
(C-9)

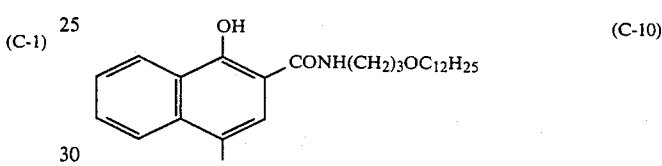
(C-10)

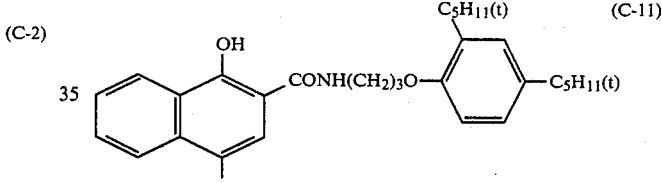
(C-11)

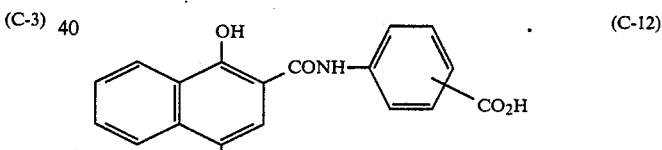
(C-12)

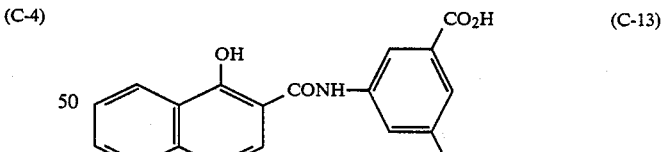
(C-13)

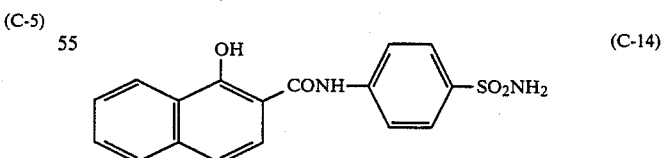
(C-14)

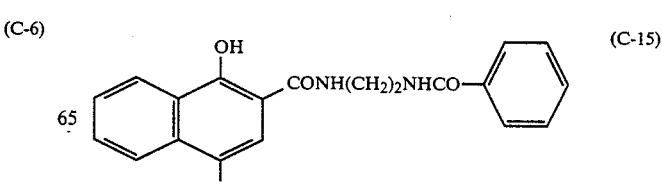
(C-15)

The connecting group represented by L is a group connecting between the substratum C and the dye portion D with a covalent bond and it also acts as a releasable group in the reaction of the oxidized product of the reducing agent with the substratum C. The connecting group C includes a divalent residue selected from the groups represented by the following general formulae:

$$-O-(\underset{R'}{\overset{R}{C}})_n-  \quad n = 0\sim3$$

$$-O-(\underset{R'}{\overset{R}{CHCH_2O}})_n-  \quad n = 1\sim2$$

$$-O-(\underset{R'}{\overset{R}{C}})_n CONH- \quad n = 0\sim3$$

$$-O-(\underset{R'}{\overset{R}{C}})_n NHCO- \quad n = 1\sim3$$

$$-O-\phenyl-NHCO-$$

$$-O-\phenyl-NHSO_2-$$

$$-O-\phenyl-CONH-$$

$$-O-\phenyl-SO_2NH-$$

$$-NHCONH-$$

$$-NHCO-(\underset{R'}{\overset{R}{C}})_n O- \quad n = 0\sim3$$

$$-S-(\underset{R'}{\overset{R}{C}})_n- \quad n = 0\sim3$$

-continued

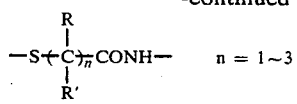 n = 1~3

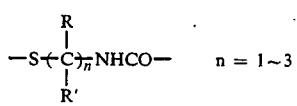 n = 1~3

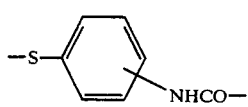

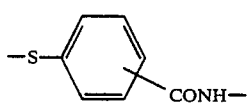

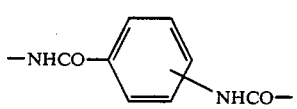

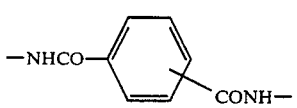

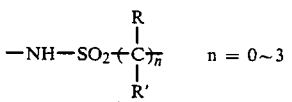 n = 0~3

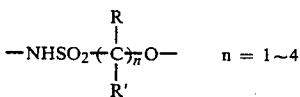 n = 1~4

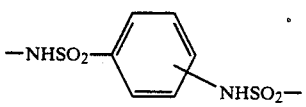

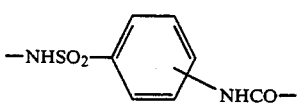

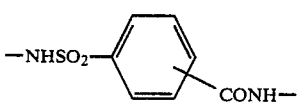

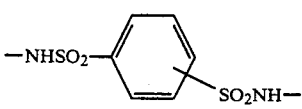

In the above formulae, R and R', which may be the same or different, each represents a hydrogen atom, a methyl group or an ethyl group, and the benzene ring may further be substituted with an alkyl group, an alkoxy group or a halogen atom.

Preferred connecting groups for L are an O-releasing type group or an S-releasing type group. Groups containing the total number of the carbon atoms of not more than 12 and having the structure shown below are particularly preferred. However, the present invention is not to be construed as being limited thereto.

 (L-1) (L-2) (L-3) (L-4)

 (L-5)

 (L-6)

 (L-7)

 (L-8)

 (L-9)

 (L-10)

 (L-11)

 (L-12) (L-13)

 (L-14)

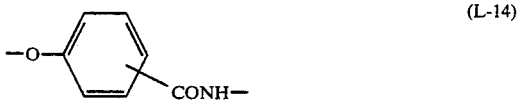 (L-15)

 (L-16)

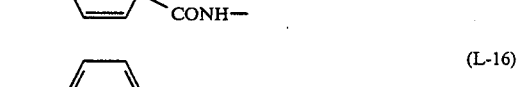 (L-17) (L-18) (L-19) (L-20)

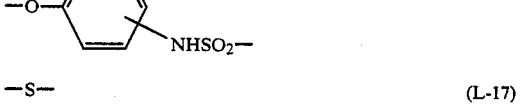 (L-21)

 (L-22)

Examples of dyes which can be used for image forming dyes include an azo dye, an azomethine dye, an anthraquinone dye, a naphthoquinone dye, a styryl dye, a quinophthalone dye and a phthalocyanine dye, etc. Preferred examples of dyes which can be used for image forming dyes include a water insoluble dye which does not contain a carboxyl group or a sulfo group. More preferred examples of the dyes are set forth below and are classified by hue.
Yellow:
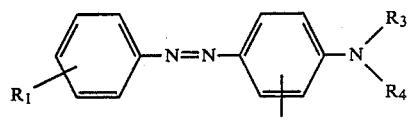
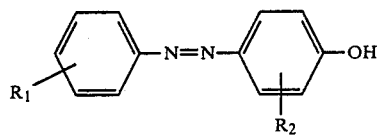
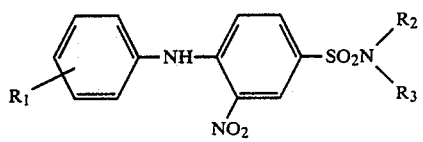
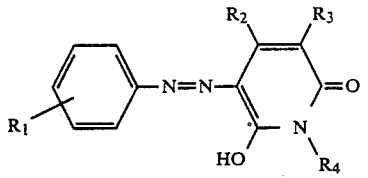
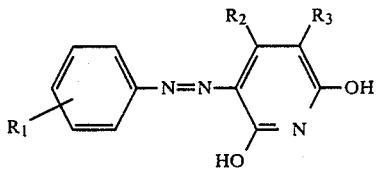
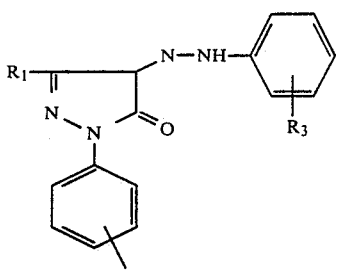
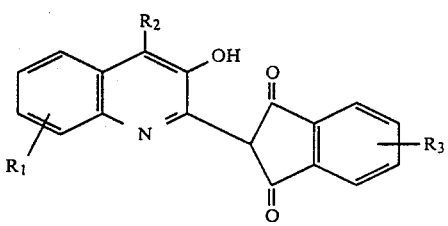
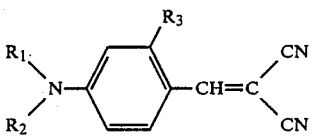
-continued
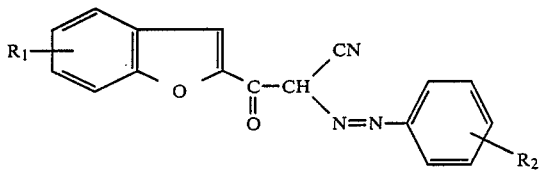
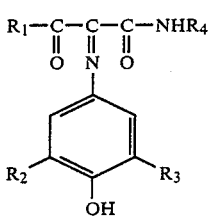
Magenta:
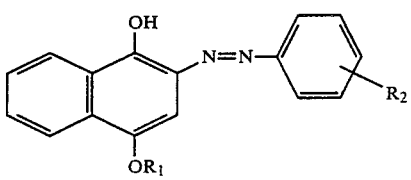
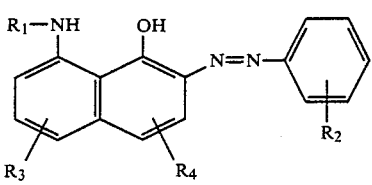
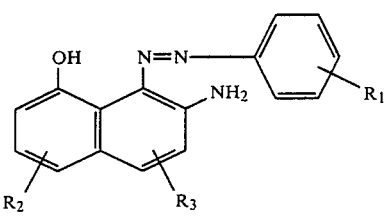
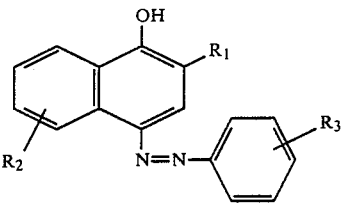
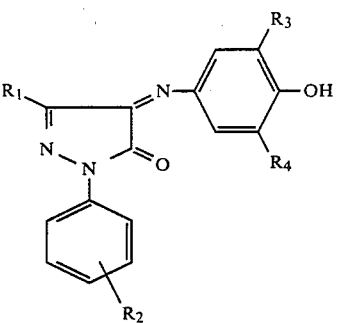

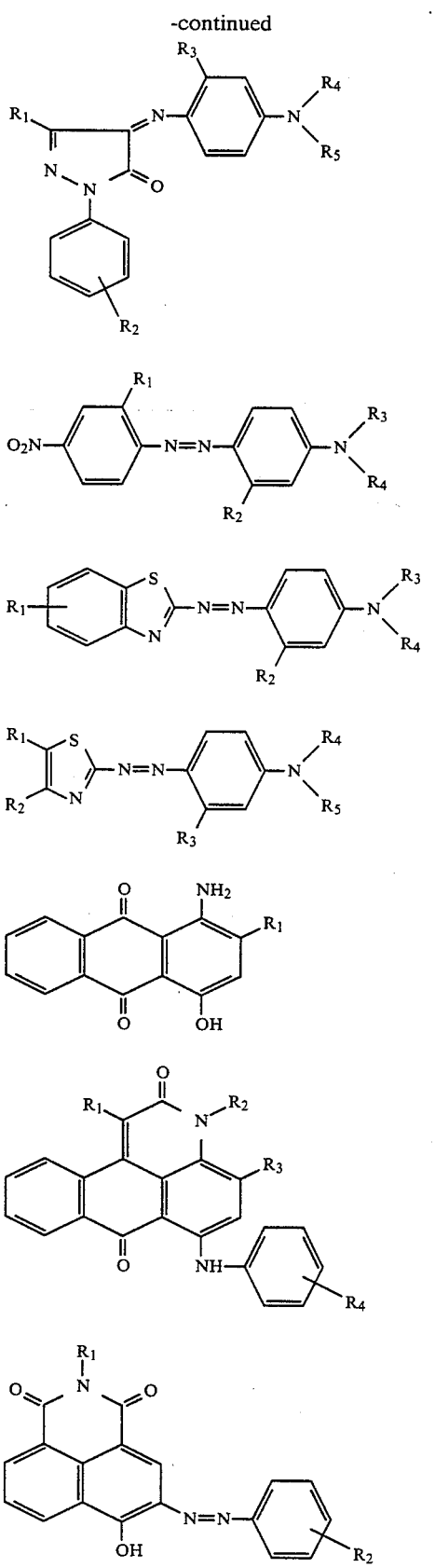
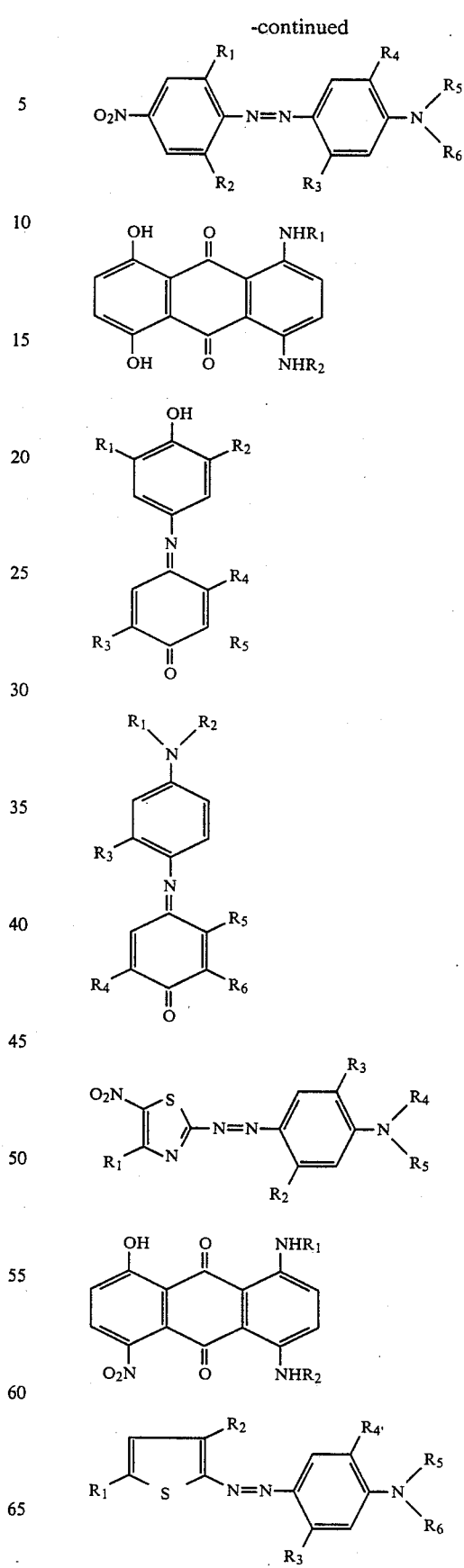
Cyan:

-continued

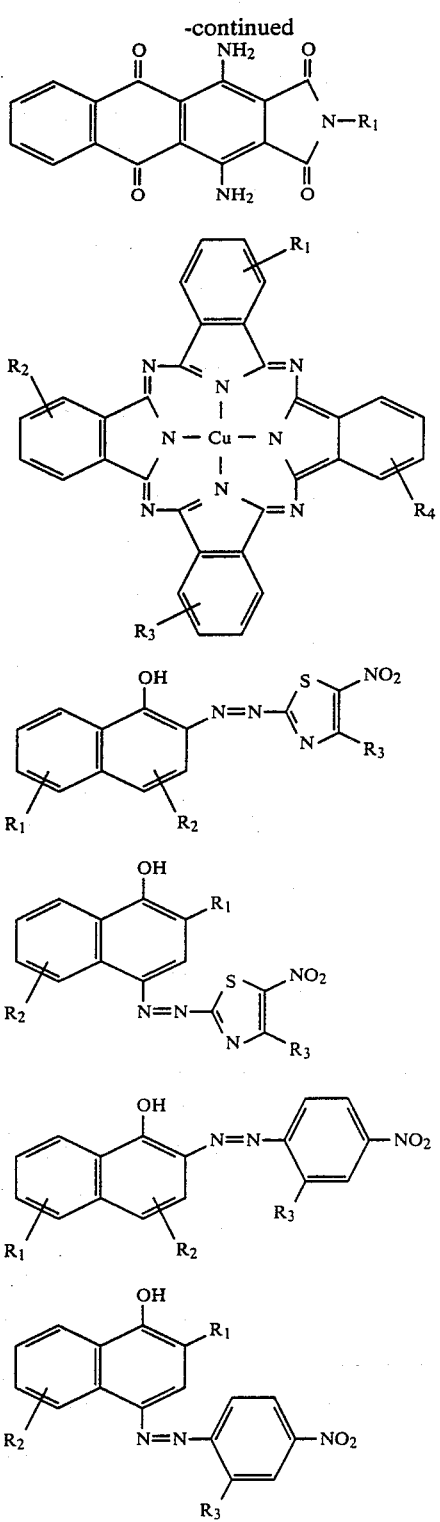

In the above formulae, $R_1$ to $R_6$, which may be the same or different, each represents hydrogen or a substituent selected from the group consisting of an alkyl group, a cycloalkyl group, an aralkyl group, an alkoxy group, an aryloxy group, an aryl group, an acylamino group, an acyl group, a cyano group, a hydroxy group, an alkylsulfonylamino group, an arylsulfonylamino group, an alkylsulfonyl group, a hydroxyalkyl group, a cyanoalkyl group, an alkoxycarbonylalkyl group, an alkoxyalkyl group, an aryloxyalkyl group, a nitro group, a halogen, a sulfamoyl group, an N-substituted sulfamoyl group, a carbamoyl group, an N-substituted carbamoyl group, an acyloxyalkyl group, an amino group, a substituted amino group, an alkylthio group and an arylthio group. It is preferred that the number of the carbon atoms of substituent represented by $R_1$ to $R_6$ is from 1 to 8, and the total number of the carbon atoms of substituents represented by $R_1$ to $R_6$ is from 1 to 18, or the substituents of $R_1$ to $R_6$ each represents hydrogen.

Characteristics required for the image forming dyes are as follows.

(1) It does not have a hydrophilic group such as a carboxylic acid group or a sulfonic acid group and can effectively diffuse by heating into a support acting as an image receiving layer.

(2) It has a hue suitable for color reproduction hue.

(3) It has a large molecular extinction coefficient.

(4) It is stable to light, heat and other additives in the system, such as the dye releasing activator.

(5) It is easily synthesized.

Specific examples of the preferred image forming dyes which satisfy the above described requirements are set forth below, but the present invention is not to be construed as being limited thereto.

Yellow:

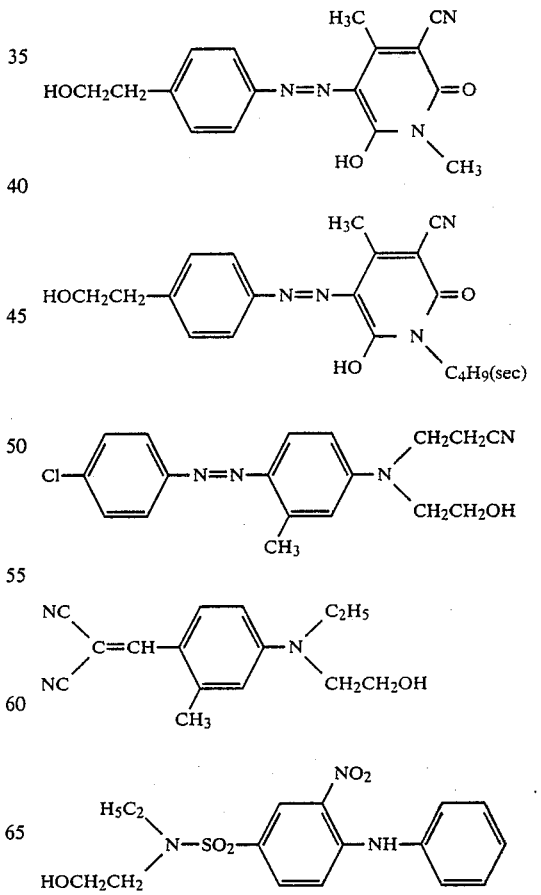

-continued

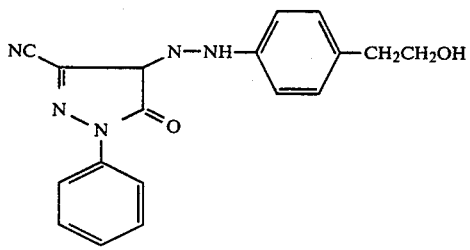

Magenta:

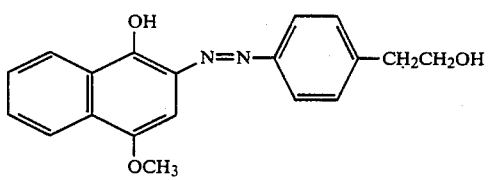

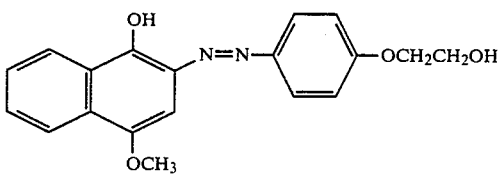

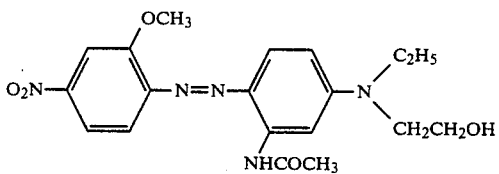

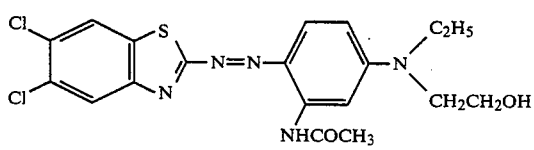

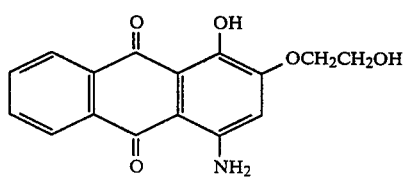

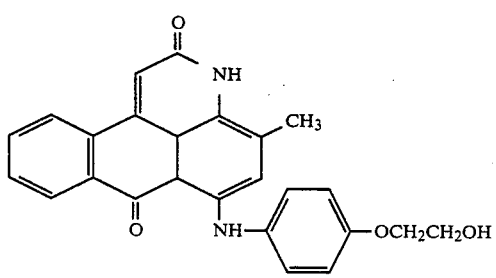

Cyan:

-continued

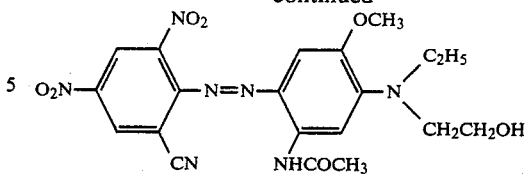

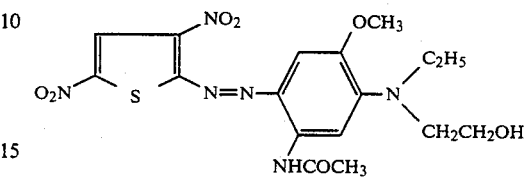

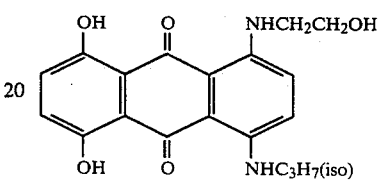

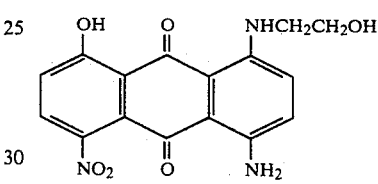

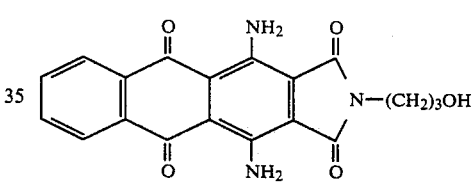

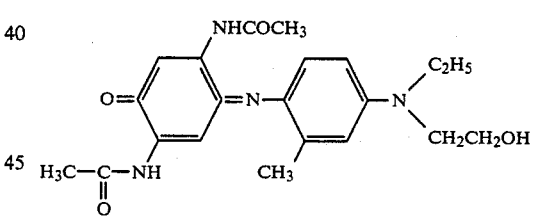

As the dye, a precursor of a dye (for example, a temporarily short-wave-shifted compound, etc.) may also be employed.

It is preferred that a dye releasing compound capable of releasing a diffusible dye is a compound which does not color an image receiving sheet. More specifically, it is preferable if only a dye released therefrom upon the reaction with the oxidized product of the reducing agent tints, in a high optical density, the images receiving sheet. Therefore, the dye releasing compound in which the substratum C has a ballast group for preventing the heat coloration of the image receiving sheet and the dye portion D does not contain a group which hinders the heat coloration of the image receiving sheet is desirable.

Specific examples of preferred dye releasing compounds are set forth below, but the present invention is not to be construed as being limited thereto.

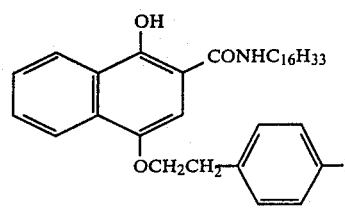 (2)
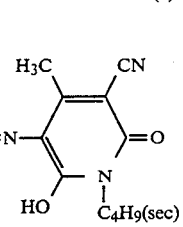
 (3)
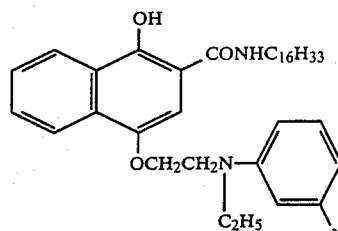 (4)
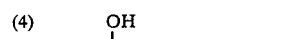 (5)
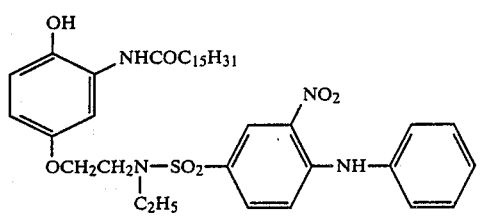 (6)
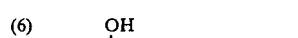 (7)
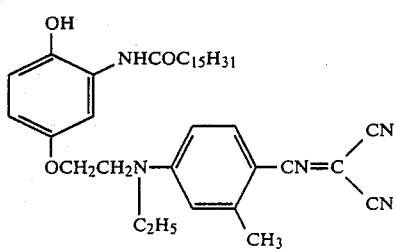 (8)
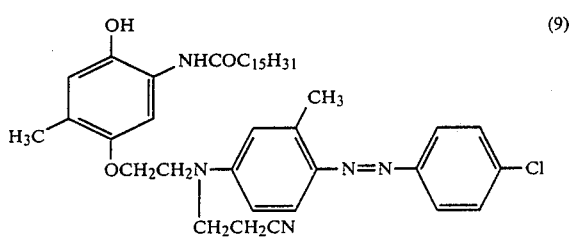 (9)
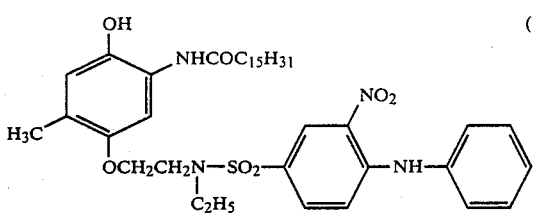 (10)
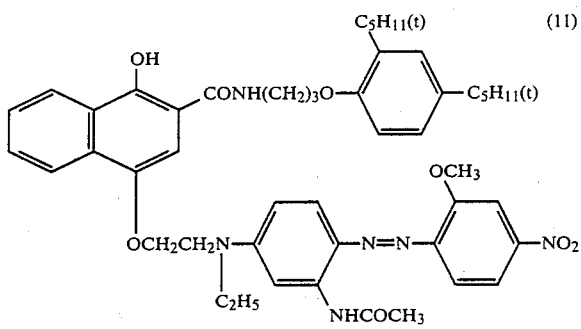 (11)
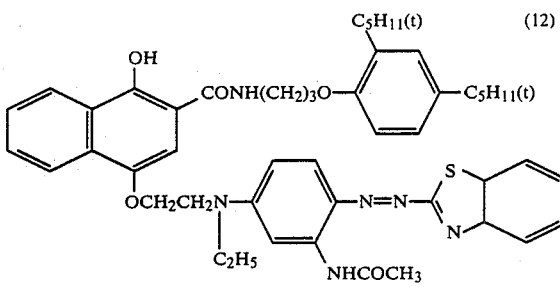 (12)
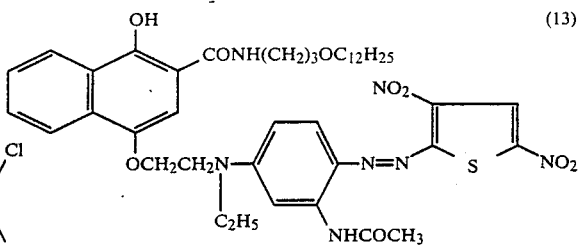 (13)

-continued
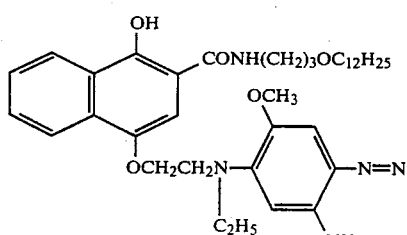 (14)
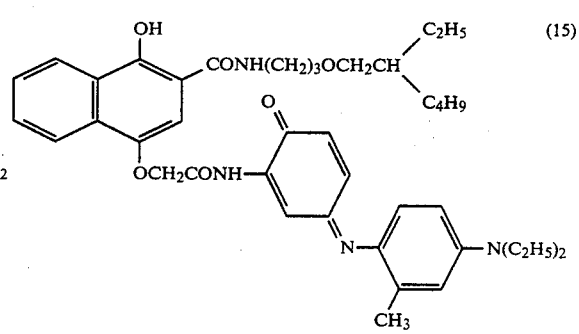 (15)
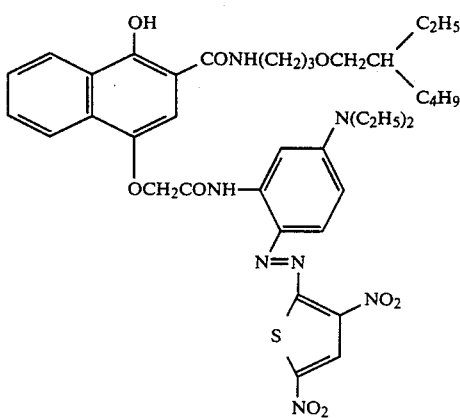 (16)
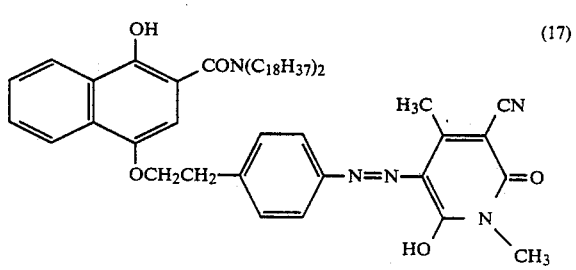 (17)
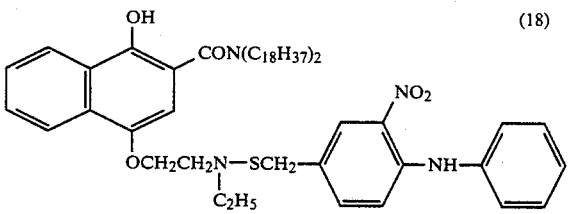 (18)
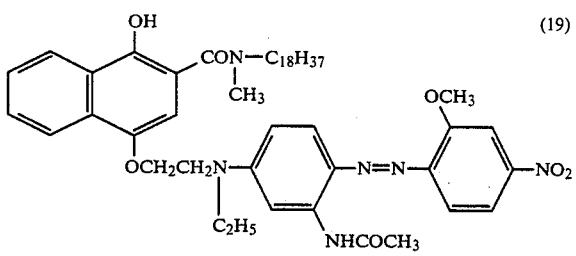 (19)
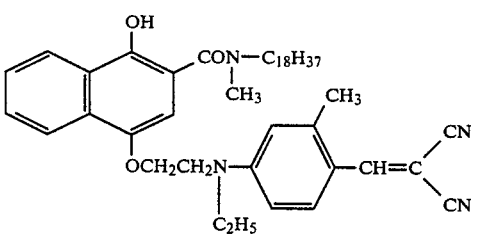 (20)
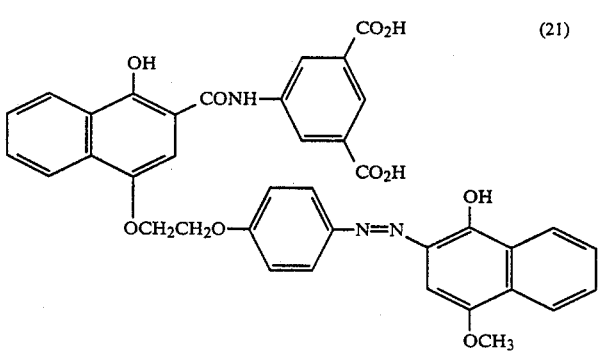 (21)
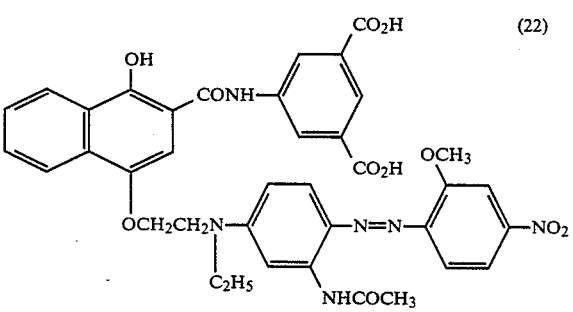 (22)
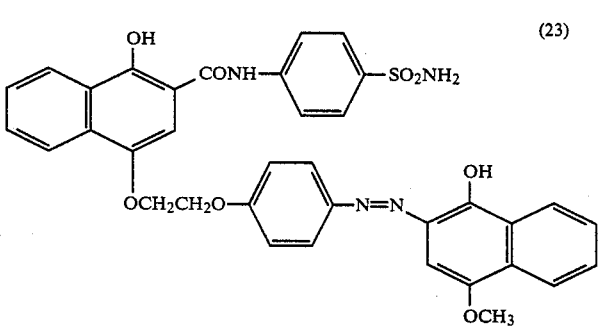 (23)

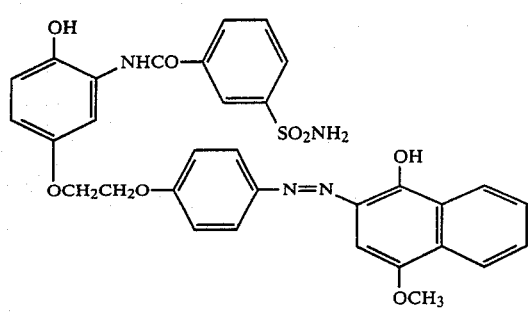

(24)

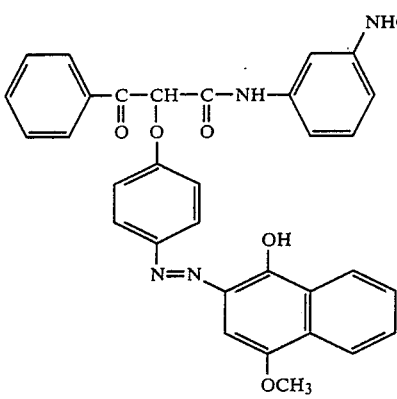

(25)

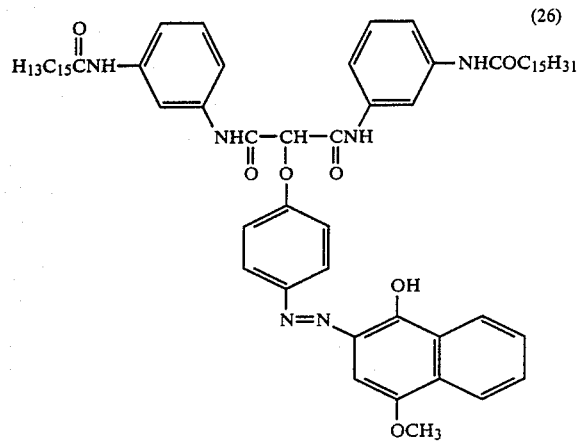

(26)

The synthesis method of the dye releasing compounds according to the present invention is described below. The dye releasing compound according to the present invention is represented by the following general formula:

B—C—L—D wherein C represents a substratum capable of bonding to the oxidized product of the reducing agent; B represents a ballast group; L represents a connecting group between C and D; and D represents a dye portion for forming an image. The dye releasing compound represented by the above described general formula can be generally synthesized according to the following two schemes:

Scheme 1:
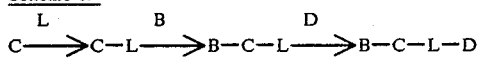

Scheme 2:
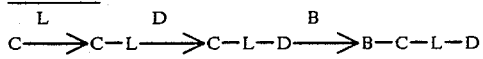

The decision on which method to be used depends on the kind of substratum C used. For example, when using a phenol type substratum or a naphthol type (both of which are particularly important), the former can be synthesized according to Scheme 2 and the latter can be synthesized according to Scheme 1. Further, the method for introducing the ballast group B is also different depending on the kind of the substratum C. For example, the introduction by acylation of an amino group at the 2-position in a phenol type substratum and the introduction by amidation of a carboxyl group (or an ester group) at the 2-position in a naphthol type compound are very general procedures. On the other hand, the introduction of the dye portion is usually carried out by a condensation reaction between a terminal group of the connecting group L and a terminal group of the dye portion D in the Scheme 1. However, this is carried out by an azo coupling method in Scheme 2.

Specific examples for the synthesis of the dye releasing compounds are set forth below, but the present invention is not to be construed as being limited thereto.

SYNTHESIS EXAMPLE 1

Synthesis of Dye Releasing Compound (1)

1-a: Synthesis of 2-(N-Hexadecylcarbamoyl)-4-{2-[N-(3-acetylaminophenyl)-N-ethylamino]ethoxy}-1-naphthol [1-a]

56 g (0.2 mol) of phenyl 1,4-dihydroxy-2-naphthoate was dissolved by heating in 100 ml of dimethylformamide and to which was added little by little 48.2 g (0.2 mol) of hexadecylamine at a temperature range between 20° C. and 30° C. After the completion of the addition, the mixture was heated at a temperature range between 70° C. and 80° C. for 3 hours. Then, 300 ml of methanol was added while the mixture was still hot and allowed to cool. The crystals thus deposited were collected by filtration and washed with methanol to obtain the compound of the formula shown below. Yield: 71 g.

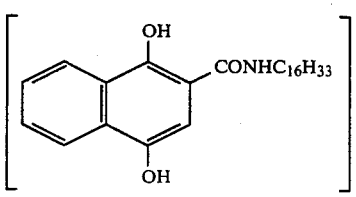

A mixture composed of 42.7 g (0.1 mol) of the crystals described above, 6.3 g of ethylene bromohydrin, 19 g of p-toluenesulfonic acid and 600 ml of toluene was refluxed by heating for 5 hours and the resulting water was removed by azeotropic distillation. After allowing to cool, toluene was distilled from the reaction mixture under a reduced pressure to concentrate. 150 ml of methanol was added thereto and the resulting crystals were collected by filtration and purified by recrystallization from ethanol to obtain the compound of the formula shown below. Yield: 44.5 g.

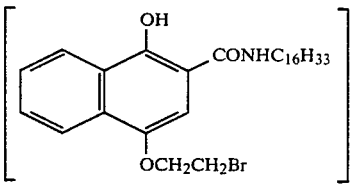

26.8 g (0.05 mol) of the above described compound, 17.8 g (0.1 mol) of 3-acetylamino-N-ethylaniline and 10.7 g (0.1 mol) of 2,6-lutidine were added to 50 ml of dimethylacetamide and the mixture was heated at a temperature range between 130° C. and 150° C. for 10 hours with stirring. After allowing to cool, 100 ml of methanol was added to the mixture and cooled with ice. The crystals thus deposited were collected by filtration and washed with water and methanol in this order to obtain 18.5 g of Compound [1-a] of the formula shown below.

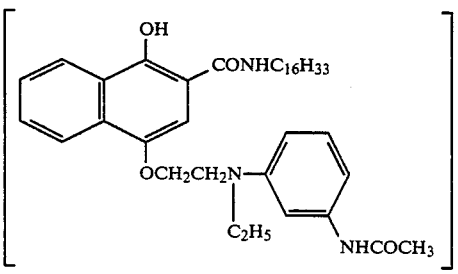

1-b: Synthesis of Dye Releasing Compound (1)

3.4 g of 2-methoxy-4-nitroaniline was diazotized in a conventional manner using 1.5 g of sodium nitrite. A mixture composed of 12.6 g of Compound [1-a], 8.2 g of sodium acetate, 100 ml of methyl Cellosolve and 20 ml of water was dissolved by heating and then cooled to 20° C. to which was added little by little the above described diazotized solution. After stirring for 30 minutes, 50 ml of water and 50 ml of methanol were added to the mixture and the resulting purple red colored crystals were collected by filtration and recrystallized from ethyl acetate to obtain 13.2 g of Dye Releasing Compound (1).

SYNTHESIS EXAMPLE 2

Synthesis of Dye Releasing Compound (2)

2-a: Synthesis of 2-(N-Hexadecylcarbamoyl)-4-[2-(p-aminophenyl)ethoxy]-1-naphthol [2-a]

A mixture composed of 42.7 g (0.1 mol) of 1,4-dihydroxy-2-(N-hexadecylcarbamoyl)naphthalene, 50.1 g (0.3 mol) of 2-(p-nitrophenyl)ethanol, 19 g of p-toluenesulfonic acid and 600 ml of toluene was refluxed by heating for 5 hours and the resulting water was removed by azeotropic distillation. After allowing to cool, toluene was distilled from the reaction mixture under a reduced pressure and the residue was dissolved in ethyl acetate. After washing with water, the thyl acetate was distilled off under a reduced pressure to concentrate and the residue was purified by a silica gel chromatography to obtain 28.2 g of 2-(N-hexadecylcarbamoyl)-4-[2-(p-nitrophenyl)ethoxy]-1-naphthol.

A mixture composed of 17.3 g (0.03 mol) of the crystals thus obtained, 2 g of ammonium chloride, 200 ml of isopropanol and 20 ml of water was heated at 50° C. Then, 12 g of a reduced iron was added little by little at a temperature range between 50° C. and 60° C. and the mixture was refluxed by heating for 1 hour. The mixture was filtered while it was still hot, the filtrate was allowed to cool and the crystals thus deposited were collected by filtration and washed with methanol to obtain 14.1 g of 2-(N-hexadecylcarbamoyl)-4-[2-(p-aminophenyl)ethoxy]-1-naphthol [2-a] of the formula shown below.

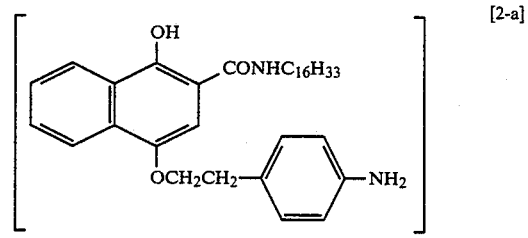

2-b: Synthesis of Dye Releasing Compound (2)

5.46 g (0.01 mol) of Compound [2-a] was dissolved by heating in 50 ml of methyl Cellosolve and to which was added 3 ml of hydrochloric acid followed by cooling to 10° C. 0.7 g of sodium nitrite was dissolved in 2 ml of water and the solution was added to the above described solution at a temperature range between 10° C. and 12° C. After stirring at 10° C. for 20 minutes, a small amount of sulfamic acid was added to the mixture and the excess nitrous acid was decomposed.

To a mixture composed of 2.06 g (0.01 mol) of 1-sec-butyl-3-cyano-6-hydroxy-4-methyl-2-pyridone, 0.4 g of sodium hydroxide, 5 g of sodium acetate, 30 ml of methyl Cellosolve and 5 ml of water was added the above described diazotized solution at a temperature range between 5° C. and 10° C. After stirring at 10° C. for 30 minutes, 30 ml of water and 30 ml of methanol were added to the mixture and the resulting yellow colored crystals were collected by filtration and recrystallized from acetonitrile to obtain 5.8 g of Dye Releasing Compound (2).

SYNTHESIS EXAMPLE 3

Synthesis of Dye Releasing Compound (3)

5.46 g (0.01 mol) of Compound [2-a] was diazotized in the same manner as described in [2-b]. 1.74 g (0.01 mol) of 4-methoxy-1-naphthol was dissolved in 20 ml of methyl Cellosolve and to the solution was added 40 ml of a 10% methanol solution of potassium hydroxide. To the solution was added the above described diazotized solution at a temperature range between 5° C. and 8° C. After stirring at 5° C. for 30 minutes, the mixture was neutralized with diluted hydrochloric acid and the resulting red purple colored precipitate was collected by filtration and recrystallized from ethyl acetate to obtain Dye Releasing Compound (3).

SYNTHESIS EXAMPLE 4

Synthesis of Dye Releasing Compound (4)

1.89 g (0.01 mol) of 2-amino-3,5-dinitrothiophene was diazotized at a temperature range between 10° C. and 15° C. in a conventional manner using nitrosyl sulfuric acid prepared from 0.75 g of sodium nitrite and 5 ml of sulfuric acid. A mixture composed of 6.32 g (0.01 mol) of Compound [1-a], 22 g of sodium acetate, 80 ml of methyl Cellosolve and 20 ml of water was dissolved by heating and then cooled to 15° C. to which was added the above described diazotized solution at a temperature range between 12° C. and 15° C. After stirring at the same temperature range for 20 minutes, 100 ml of water and 50 ml of methanol were added to the mixture and the resulting dark blue colored crystals were collected by filtration and washed with water. Upon recrystallization from acetonitrile the green crystals of Dye Releasing Compound (4) were obtained.

SYNTHESIS EXAMPLE 5

Synthesis of Dye Releasing Compound (5)

5-a: Synthesis of 2-Pentadecyl-5-hydroxybenzoxazole [5-a]

83.8 g (0.2 mol) of 1,4-diethoxy-2-hexadecanoylaminobenzene prepared from 2,5-diethoxyaniline and hexadecanoyl chloride was dissolved in 500 ml of chloroform and to the solution was added dropwise 100 g of boron tribromide at a temperature range between 5° C. and 10° C. After stirring at room temperature for 6 hours, 50 g of ice and 100 ml of water were added to the mixture and chloroform was distilled off under a reduced pressure. To the residue was added 100 ml of methanol, the resulting precipitate was collected by filtration to obtain 78 g of 2-hexadecanoylaminohydroquinone.

A mixture composed of 36.3 g (0.1 mol) of the above described compound, 19 g of p-toluenesulfonic acid and 300 ml of toluene was refluxed by heating for 3 hours and the resulting water was removed by azeotropic distillation. After allowing to cool, 100 ml of water and 100 ml of ethyl acetate were added to the mixture and the organic layer was separated which was washed with water and dried. The solvent was distilled off under a reduced pressure and the residue was recrystallized from n-hexane to obtain 27 g of 2-pentadecyl-5-hydroxybenzoxazole [5-a].

5-b: Synthesis of Dye Releasing Compound (5)

16.8 g (0.1 mol) of 2-methoxy-4-nitroaniline was diazotized in a conventional manner using 7.0 g of sodium nitrite and subjected to coupling with 17.9 g (0.1 mol) of N-ethyl-N-hydroxyethyl-m-toluidine to obtain 34.4 g of 3-methyl-4-(2-methoxy-4-nitrophenylazo)-N-ethyl-N-hydroxyethylaniline. 17.9 g (0.05 mol) of the compound thus obtained was added to 50 ml of pyridine and then to the mixture was added little by little 29 g of p-toluenesulfonyl chloride at a temperature range between 10° C. and 15° C. After the completion of the addition, the mixture was stirred at room temperature for 2 hours, then the reaction solution was poured into cool diluted hydrochloric acid and the resulting red colored precipitate was collected by filtration. The crude product was recrystallized from diluted acetone to obtain 14.2 g of 3-methyl-4-(2-methoxy-4-nitrophenylazo)-N-ethyl-N-toluenesulfonyloxyethylaniline [5-b].

A mixture composed of 6.9 g (0.02 mol) of Compound [5-a], 10.3 g (0.02 mol) of Compound [5-b], 2.8 g of anhydrous potassium carbonate and 40 ml of dimethylacetamide was heated on a steam bath for 10 hours with stirring. After allowing to cool, 30 ml of 6N hydrochloric acid and 50 ml of isopropanol were added and the mixture was heated at a temperature range between 40° C. and 50° C. for 1 hour. After allowing to cool, the red colored crystals thus deposited were collected by filtration and recrystallized from acetonitrile to obtain 7.5 g of Dye Releasing Compound (5).

The dye releasing compound which releases a diffusible dye according to the present invention can be used in an amount of a certain concentration range. Generally, a suitable concentration range is from about 0.01 mol to about 4 mols of the dye releasing compound per mol of the organic silver salt oxidizing agent. A particularly suitable amount of the dye releasing compound in the present invention is in a concentration range of about 0.05 mol to about 1 mol per mol of the organic silver salt oxidizing agent.

The photographic silver halide used in the present invention can be employed in a range from 0.005 mol to 5 mols and, preferably, from 0.005 mol to 1.0 mol, per mol of the organic silver salt oxidizing agent.

Examples of silver halide include silver chloride, silver chlorobromide, silver chloroiodide, silver bromide, silver iodobromide, silver chloroiodobromide and silver iodide, etc.

The particle size of the silver halide used is from 0.001 $\mu$m to 2 $\mu$m and, preferably, from 0.001 $\mu$m to 1 $\mu$m.

The silver halide used in the present invention may be employed as is, but it may be chemically sensitized with a chemical sensitizing agent such as a compound containing sulfur, selenium or ellurium, etc., or a compound containing gold, platinum, palladium, rhodium or iridium, etc., a reducing agent such as a tin halide, etc., or a combination thereof. The details of these procedures are described in T. H. James, *The Theory of the Photographic Process*, Fourth Edition, Chapter 5, pages 149 to 169.

The organic silver salt oxidizing agent which can be used in the present invention is a silver salt which is comparatively stable to light and which forms a silver image by reacting with the reducing agent, when it is heated to a temperature of above 80° C. and, preferably, above 100° C. in the presence of exposed silver halide.

Examples of such organic silver salt oxidizing agents include the following compounds.

A silver salt of an organic compound having a carboxy group. Typical examples thereof include a silver salt of an aliphatic carboxylic acid and a silver salt of an aromatic carboxylic acid.

Examples of the silver salts of aliphatic carboxylic acids include silver behenate, silver stearate, silver oleate, silver laurate, silver caprate, silver myristate, silver palmitate, silver maleate, silver fumarate, silver tartarate, silver furoate, silver linolate, silver oleate, silver adipate, silver sebacate, silver succinate, silver acetate, silver butyrate and silver camphorate, etc. These silver salts which are substituted with a halogen atom or a hydroxyl group are also effectively used.

Examples of the silver salts of aromatic carboxylic acid and other carboxyl group containing compounds include silver benzoate, a silver substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenylbenzoate, etc., silver gallate, silver tannate, silver phthalate, silver terephthalate, silver salicylate, silver phenylacetate, silver pyromellitate, a silver salt of 3-carboxymethyl-4-methyl-4-thiazoline-2-thione or the like as described in U.S. Pat. No. 3,785,830, and a silver salt of an aliphatic carboxylic acid containing a thioether group as described in U.S. Pat. No. 3,330,663, etc.

In addition, a silver salt of a compound containing a mercapto group or a thione group and a derivative thereof can be used.

Examples of these compounds include a silver salt of 3-mercapto-4-phenyl-1,2,4-triazole, a silver salt of 2-mercaptobenzimidazole, a silver salt of 2-mercapto-5-aminothiadiazole, a silver salt of 2-mercaptobenzothiazole, a silver salt of 2-(S-ethylglycolamido)benzothiazole, a silver salt of thioglycolic acid such as a silver salt of an S-alkyl thioglycolic acid (wherein the alkyl group has from 12 to 22 carbon atoms) as described in Japanese Patent Application (OPI) No. 28221/73 (the term "OPI" as used herein refers to a "published unexamined Japanese Patent application"), a silver salt of dithiocarboxylic acid such as a silver salt of dithioacetic acid, a silver salt of thioamide, a silver salt of 5-carboxyl-1-methyl-2-phenyl-4-thiopyridine, a silver salt of mercaptotriazine, a silver salt of 2-mercaptobenzoxazole, a silver salt of mercaptooxadiazole, a silver salt as described in U.S. Pat. No. 4,123,274, for example, a silver salt of 1,2,4-mercaptotriazole derivative such as a silver salt of 3-amino-5-benzylthio-1,2,4-triazole, a silver salt of thione compound such as a silver salt of 3-(2-carboxyethyl)-4-methyl-4-thiazoline-2-thione as described in U.S. Pat. No. 3,301,678, and the like.

Further, a silver salt of a compound containing an imino group can be used. Examples of these compounds include a silver salt of benzotriazole and a derivative thereof as described in Japanese Patent Publication Nos. 30270/69 and 18416/70, for example, a silver salt of benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are examples of the organic metal salt oxidizing agent capable of being used in the present invention.

The mechanism of the heat development process under heating in the present invention is not entirely clear, but it is believed to be as follows.

When the photographic material is exposed to light, a latent image is formed in a photographic silver halide. This phenomenon is described in T. H. James, *The Theory of the Photographic Process*, Third Edition, pages 105 to 148.

When the photographic material is heated, the reducing agent reduces the organic metal salt oxidizing agent or both the silver halide and the organic metal salt oxidizing agent in the presence of the latent image nuclei as a catalyst with the aid of an alkali agent released by heating to form silver or metal, while it is oxidized itself. The oxidized product of the reducing agent causes a coupling reaction with the dye releasing compound whereby a dye is released.

The silver halide and the organic silver salt oxidizing agent which form a starting point of development should be present within a substantially effective distance.

For this purpose, it is desired that the silver halide and the organic silver salt oxidizing agent are present in the same layer.

The silver halide and the organic metal salt oxidizing agent which are separately formed in a hydrophobic binder can be mixed prior to use to prepare a coating solution, but it is also effective to blend both of them in a ball mill for a long period of time. Further, it is effective to use a process which comprises adding a halogen containing compound to the organic silver salt oxidizing agent prepared to form silver halide using silver of the organic silver salt oxidizing agent.

Methods of preparing these silver halide and organic silver salt oxidizing agents and manners of blending them are described in *Research Disclosure*, No. 17029, Japanese Patent Application (OPI) Nos. 32928/75 and 42529/76, U.S. Pat. No. 3,700,458, and Japanese Patent Application (OPI) Nos. 13224/74 and 17216/75.

A suitable coating amount of the photographic silver halide and the organic silver salt oxidizing agent employed in the present invention is in a total of from 50 mg to 10 g/m$^2$ calculated as an amount of silver.

The photographic silver halide and the organic silver salt oxidizing agent used in the present invention are prepared in the binder as described below. Further, the dye releasing compound is dispersed in the binder described below.

The binder which can be used in the present invention can be employed individually or in a combination of two or more. Both of a hydrophilic polymer and a hydrophobic polymer can be used as the binder according to the present invention. The typical hydrophilic binder is a transparent or translucent hydrophilic colloid, examples of which include a natural substance, for example, protein such as gelatin, a gelatin derivative, a cellulose derivative, a polysaccharide such as starch, gum arabic, etc., and a synthetic polymer, for example, a water-soluble polyvinyl compound such as polyvinyl pyrrolidone, acrylamide polymer, etc. Another example of the synthetic polymer compound is a dispersed vinyl compound in a latex form which is used for the purpose of increasing dimensional stability of a photographic material.

The hydrophobic polymer binder which can be used in the present invention is a transparent synthetic polymer, examples of which include those described in U.S. Pat. Nos. 3,142,586, 3,143,386, 3,062,674, 3,220,844, 3,287,289 and 3,411,911. Examples of the effective polymers include a water-insoluble polymer composed of a monomer such as an alkyl acrylate, an alkyl methacrylate, acrylic acid, a sulfoalkyl acrylate or a sulfoalkyl methacrylate, etc., and a polymer having cyclic sulfobetaine unit as described in Canadian Pat. No. 774,054. Examples of preferred polymers include polyvinyl butyral, polyacrylamide, cellulose acetate butyrate, cellulose acetate propionate, polymethyl methacrylate, polyvinyl pyrrolidone, polystyrene, ethyl cellulose, polyvinyl chloride, chlorinated rubber, polyisobutylene, a butadiene-styrene copolymer, a vinyl chloride-vinyl acetate copolymer, a vinyl chloride-vinyl acetate-maleic acid copolymer, polyvinyl alcohol, polyvinyl acetate, benzyl cellulose, acetyl cellulose, cellulose propionate and cellulose acetate phthalate, etc. Among these polymers, the use of polyvinyl butyral, polyvinyl acetate, ethyl cellulose, polymethyl methacrylate and cellulose acetate butyrate are particularly preferred. If necessary, two or more of them may be used as a mixture.

A support capable of receiving a dye or an organic high molecular weight compound capable of receiving a dye on a support used in the present invention should be able to uphold the photographic light-sensitive layer and simultaneously receive the dye released from the dye releasing compound during the heat development proceudre. The support or the organic high molecular weight compound described above which is suitable for these purposes is composed of a heat-resisting organic high molecular weight compound having a glass transition temperature of from 40° C. to 250° C. which is used in the form of a film or a resin plate. The mechanism by which the dye released from the dye releasing compound gets into the support is not entirely clear. However, it is generally believed that the heat kinetics of a polymer chain are increased at a treatment temperature above the glass transition temperature and the dye can get into the thus-formed gap in the molecular chain. Therefore, the dye is distinguished from the dye releasing compound and only dye can get into the support to form a clear image by the use of the support composed of an organic high molecular weight compound having a glass transition temperature of from 40° C. to 250° C.

Examples of the organic high molecular weight compounds used in the present invention include polystyrene having a molecular weight of 2,000 to 85,000, a polystyrene derivative having a substituent containing not more than 4 carbon atoms, polyvinyl cyclohexane, polydivinyl benzene, polyvinyl pyrrolidone, polyvinyl carbazole, polyalkyl benzene, polyvinyl alcohol, a polyacetal such as polyvinyl formal, polyvinyl butyral, etc., polyvinyl chloride, chlorinated polyethylene, polytrichlorofluoroethylene, polyacrylonitrile, poly-N,N-dimethyl allylamide, a polyacrylate having a p-cyanophenyl group, a pentachlorophenyl group and a 2,4-dichlorophenyl group, polyacryl chloroacrylate, polymethyl methacrylate, polyethyl methacrylate, polypropyl methacrylate, polyisopropyl methacrylate, polyisobutyl methacrylate, polytertiary butyl methacrylate, polycyclohexyl methacrylate, polyethyleneglycol dimethacrylate, poly-2-cyanoethyl methacrylate, a polyester such as polyethylene terephthalate, etc., polysulfone, bisphenol A polycarbonate, a polycarbonate, polyanhyride, a polyamide, a cellulose acetate. Further, synthetic polymers having a glass transition temperature of from 40° C. to 250° C. as described in J. Brandrup and E. H. Immergut, *Polymer Handbook*, Second Edition (John Wiley & Sons) are useful. These high molecular weight compounds can be used individually or as a copolymer composed of a combination of two or more thereof.

Examples of particularly preferred supports include a cellulose acetate film such as cellulose triacetate, cellulose diacetate, etc., a polyamide film such as a combination of heptamethylenediamine and terephthalic acid, a combination of fluorenedipropylamine and adipic acid, a combination of hexamethylenediamine and diphenic acid, a combination of hexamethylenediamine and isophthalic acid, etc., a polyester film such as a combination of diethyleneglycol and diphenylcarboxylic acid, a combination of bis-p-carboxyphenoxy butane and ethyleneglycol, etc., a polyethylene terephthalate film and a polycarbonate film. These films may be modified. For example, a polyethylene terephthalate film modified using cyclohexanedimethanol, isophthalic acid, methoxypolyethyleneglycol, 1,2-dicarbomethoxy-4-benzenesulfonic acid, etc., as a modifying agent is effectively used.

The support can be composed of a single layer or two or more layers. Further, the support may contain titanium dioxide or have thereon a portion or a layer containing titanium dioxide to form a white reflective layer. Moreover, the support which can be used in the present invention may be glass, paper, metal, etc., having coated thereon a layer composed of the above described organic high molecular weight compound.

The reducing agent which can be used in the present invention is oxidized by the organic silver salt oxidizing agent to form an oxidized product capable of reacting with the dye releasing compound and releasing a dye to form a color image. An example of an effectively used reducing agent having such an ability is a color developing agent capable of forming an image upon oxidative coupling. Examples of the reducing agents used in the heat-developapble color photographic material according to the present invention include a p-phenylenediamine type color developing agent including N,N-diethyl-3-methyl-p-phenylenediamine which is a typical example as described in U.S. Pat. No. 3,531,286. Further, an example of an effective reducing agent is an aminophenol as described in U.S. Pat. No. 3,761,270. Of the aminophenol type reducing agents, 4-amino-2,6-dichlorophenol, 4-amino-2,6-dibromophenol, 4-amino-2-methylphenol sulfate, 4-amino-3-methylphenol sulfate, 4-amino--2,6-dichlorophenol hydrochloride, etc., are particularly useful. Further, a 2,6-dichloro-4-substituted sulfonamidophenol, and a 2,6-dibromo-4 -substituted sulfonamidophenol, etc., as described in *Research Disclosure*, Vol. 151, No. 15108 and U.S. Pat. No. 4,021,240 are also useful. In addition to the phenol type reducing agents described above, a naphthol type reducing agent, for example, a 4-aminonaphthol derivative and a 4-substituted sulfonamidonaphthol derivative is useful. Moreover, a generally applicable color developing agent, an aminohydroxy pyrazole derivative as described in U.S. Pat. No. 2,895,825, an aminopyrazoline derivative as described in U.S. Pat. No. 2,892,714, a hydrazone derivative as described in *Research Disclosure*, pages 227 to 230 and 236 to 240, Nos. RD-19412 and RD-19415 (June, 1980) may also be used. These reducing agents can be used individually or in a combination of two or more thereof.

In addition to the above described reducing agents, a reducing agent described below may be used as an auxiliary developing agent. Examples of useful auxiliary developing agents include hydroquinone, an alkyl substituted hydroquinone such as tertiary butylhydroquinone or 2,5-dimethylhydroquinone, etc., a catechol, a pyrogallol, a halogen substituted hydroquinone such as chlorohydroquinone or dichlorohydroquinone, etc., an alkoxy substituted hydroquinone such as methoxyhydroquinone, etc., and a polyhydroxybenzene derivative such as methyl hydroxynaphthalene, etc. Further, methyl gallate, ascorbic acid, an ascorbic acid derivative, a hydroxylamine such as N,N'-di(2-ethoxyethyl)-hydroxylamine, etc., a pyrazolidone such as 1-phenyl-3-pyrazolidone or 4-methyl-4-hydroxymethyl-1-phenyl-3-pyrazolidone, etc., a reductone and a hydroxy tetronic acid are also useful.

The reducing agent can be used in a certain range of concentration. In general, a suitable concentration range of the reducing agent is from about 0.1 mol to about 4 mols of the reducing agent per mol of the oxidizing agent. A suitable concentration of the reducing agent used in the present invention is generally from about 0.1 mol to about 20 mols of the reducing agent per mol of the oxidizing agent.

In the heat-developable color photographic material of the present invention, various kinds of bases and base releasing agents can be employed. By the use of the base or base releasing agent, a desirable color image can be obtained at a lower temperature.

Examples of preferred bases are amines which include a trialkylamine, a hydroxyalkylamine, an aliphatic polyamine, an N-alkyl substituted aromatic amine, an N-hydroxyalkyl substituted aromatic amine and a bis[p-(dialkylamino)phenyl]methane. Further, betaine tetramethylammonium iodide and diaminobutane dihydrochloride as described in U.S. Pat. No. 2,410,644, and urea and an organic compound including an amino acid such as 6-aminocaproic acid as described in U.S. Pat. No. 3,506,444 are useful. The base releasing agent is a compound or a mixture which releases a basic component by heating, and the basic component is capable of activating the photographic material. Examples of typical base releasing agents are described in British Pat. No. 998,949. Preferred base releasing agents include a salt of a carboxylic acid and an organic base, and examples of suitable carboxylic acids include trichloroacetic acid and trifluoroacetic acid, etc., and examples of suitable bases include guanidine, piperidine, morpholine, p-toluidine and 2-picoline, etc. Guanidine trichloroacetate as described in U.S. Pat. No. 3,220,846 is particularly preferred. Further, an aldonic amide as described in Japanese Patent Application (OPI) No. 22625/75 are preferably used because it decomposes at a high temperature to form a base.

Further, in the heat-developable color photographic material of the present invention, many known compounds which activate development and simultaneously stabilize the image can be effectively used. Of these compounds, an isothiuronium including 2-hydroxyethylisothiuronium trichloroacetate as described in U.S. Pat. No. 3,301,678, a bisisothiuronium including 1,8-(3,6-dioxaoctane)-bis(isothiuronium trifluoroacetate), etc., as described in U.S. Pat. No. 3,669,670, a thiol compound as described in West German Patent Application (OLS) No. 2,162,714, a thiazolium compound such as 2-amino-2-thiazolium trichloroacetate and 2-amino-5-bromoethyl-2-thiazolium trichloroacetate, etc., as described in U.S. Pat. No. 4,012,260, a compound having α-sulfonylacetate as an acid part such as bis(2-amino-2-thiazolium)methylene-bis(sulfonylacetate), 2-amino-2-thiazolium phenylsulfonylacetate, etc., as described in U.S. Pat. No. 4,060,420, and a compound having 2-carboxyamide as an acid part as described in U.S. Pat. No. 4,088,496, and the like are preferably used.

These compounds or mixtures thereof can be used in a wide range of amounts. It is preferable to use them in a range of 1/100 times to 10 times and, particularly 1/20 times to 2 times by molar ratio based on silver.

In the heat-developable color photographic material of the present invention, a diffusion accelerator can be incorporated. The term "diffusion accelerator" means a non-hydrolyzable organic compound which is solid at an ambient temperature but melts at a temperature lower than the heat treatment temperature to be used and gets into the support during the heat treatment. Examples of preferred diffusion accelerators include diphenyl, o-phenylphenol, phenol, resorcinol and pyrogallol, etc. As the diffusion accelerator, a compound which is used as a thermal solvent can be used. The term "thermal solvent" means a non-hydrolyzable organic material which is solid at an ambient temperature but melts together with other components at a temperature of heat treatment or a temperature lower than the heat treatment temperature. As the thermal solvent, a compound which becomes a solvent for the developing agent and a compound having a high dielectric constant which accelerate physical development of the silver salt, etc., are useful. Preferred examples of the thermal solvents include a polyglycol as described in U.S. Pat. No. 3,347,675, for example, polyethylene glycol having an average molecular weight of 1,500 to 20,000, a derivative of polyethylene oxide such as an oleic acid ester thereof, etc., beeswax, monostearin, a compound having a high dielectric constant which has an —$SO_2$— or —CO— group such as acetamide, succinimide, ethyl-carbamate, urea, methylsulfonamide, ethylene carbonate, a polar substance as described in U.S. Pat. No. 3,667,959, lactone of 4-hydroxybutanoic acid, methyl-sulfinylmethane, tetrahydrothiophene-1,1-dioxide, and 1,10-decanediol, methyl anisate, biphenyl suberate, etc., as described in *Research Disclosure*, pages 26 to 28 (December, 1976), etc.

In the present invention, though it is not so necessary to further incorporate a substance or a dye for preventing irradiation or halation in the photographic material, since the dye releasing compound is colored, it is possible to add a filter dye or a light absorbing material as described in Japanese Patent PUblication No. 3692/73, U.S. Pat. Nos. 3,253,921, 2,527,583 and 2,956,879, etc., in order to further improve sharpness. Preferably, these dyes have a thermal bleaching property. For example, dyes as described in U.S. Pat. Nos. 3,769,019, 3,745,009 and 3,615,432 are preferred.

The photographic material according to the present invention may contain, if desired, various additives known for the heat-developable photographic material and may have an antistatic layer, an electrically conductive layer, a protective layer, an intermediate layer, an antihalation layer and a strippable layer, etc., in addition to the photographic layer. As the additives, those described in *Research Disclosure*, Vol. 170, No. 17029 (June, 1978), for example, a plasticizer, a dye for improving sharpness, an antihalation dye, a sensitizing dye, a matting agent, a surface active agent, a fluorescent whitening agent, a fade preventing agent, etc., may be used.

The protective layer, the intermediate layer, the subbing layer, the back layer and other layers can be produced by preparing each coating solution and applying them in order to the support by various coating methods such as a dip coating method, an air-knife coating method, a curtain coating method, a hopper coating method as described in U.S. Pat. No. 2,681,294 and drying to prepare the light-sensitive material, in a manner similar to the heat-developable photographic layer according to the present invention. If desired, two or more layers may be applied at the same time by the method as described in U.S. Pat. No. 2,761,791 and British Pat. No. 837,095.

For the heat-developable photographic material of the present invention, various means for exposing to light can be used. A latent image is obtained by image-wise exposure to radiant rays including visible rays. Generally, a light source used for conventional color prints can be used, examples of which include a tungsten lamp, a mercury lamp, a halogen lamp such as an iodine lamp, etc., a xenon lamp, a laser light source, a CRT light source, a fluorescent tube, a light-emitting diode, etc.

As the original, not only a line drawing but also a photograph having gradation may be used. It is also possible to take a photograph of a portrait or a landscape by means of a camera. Printing from the original may be carried out by contact printing by super-imposing the original on the photographic material or may be carried out by reflection printing or enlargement printing.

Further, it is possible to carry out the printing of an image photographed by a videocamera or image information sent from a television broadcasting station by displaying it directly on CRT or FOT and forcusing the resulting image on the heat-developable photographic material by contacting therewith or by means of a lens.

Recently, LED (light-emitting diode) which has been greatly improved is utilized as an exposure means or display means for various apparatus and devices. It is difficult to produce LED which effectively emits blue light. In this case, in order to reproduce the color image, three kinds of LED consisting of those emitting each green light, red light and infrared light are used, and the photographic layers to be sensitized to these lights are produced so as to release a yellow dye, a magenta dye and a cyan dye, respectively. Namely, the photographic material is produced in such a construction that the green-sensitive part (layer) contains a yellow dye releasing compound, the red-sensitive part (layer) contains a magenta dye releasing compound and the infrared-sensitive part (layer) contains a cyan dye releasing compound. Other combinations can be utilized, if desired.

Besides the above described methods for contact exposure or projection of the original, there can be used a method of exposure wherein the original illuminated by a light source is stored in a memory of a leading computer by means of a light-receiving element such as a phototube or CCD, etc., the information is, if desired, subjected to processing, the so-called image treatment, and the resulting image information is reproduced on CRT and utilized as an imagelike light source or three kinds of LED are emitted according to the processed information.

After the heat-developable color photographic material is exposed to light, the latent image thus-obtained can be developed by heating the whole material at a suitably elevated temperature, for example, from about 80° C. to about 250° C. for from about 0.5 second to about 300 seconds. Any higher temperature or lower temperature can be utilized by prolonging or shortening the heating time, if it is within the above-described range. Particularly, a temperature range from about 110° C. to about 160° C. is useful. As a heating means, a simple heat plate, an iron, a heat roller or analogues thereof may be used.

According to the present invention, a color image is composed of dyes diffused into a support, therefore, a visible image can be obtained by (1) peeling apart the emulsion layer from the support after heat development or (2) providing a white reflective layer containing titanium dioxide dispersed therein between the support and the emulsion layer. In order to peel apart the emulsion layer, various methods can be employed. For example, the emulsion layer can be mechanically peeled apart using an adhesive tape. Alternatively, the emulsion layer can be removed by dissolving using a solvent such as ethyl alcohol. Further, a method in which a stripping layer is provided between the emulsion layer and the support is effectively used. The stripping layer is composed of an organic material which has a low affinity to one of a binder of the emulsion layer and a synthetic polymer composed of the support or both of them.

The present invention will be explained in greater detail with reference to the following examples, but the present invention should not be construed as being limited thereto.

EXAMPLE 1

A silver benzotriazole emulsion containing photographic silver bromide was prepared in the following manner.

| (A) | Benzotriazole | 12 g |
| --- | --- | --- |
|     | Isopropyl alcohol | 200 ml |
| (B) | AgNO$_3$ | 17 g |
|     | H$_2$O | 50 ml |
| (C) | LiBr | 2.1 g |
|     | Ethanol | 20 ml |

Solution B was added to Solution A with stirring at 40° C. Solution A became turbid and silver salts of benzotriazole were formed.

To the resulting solution, Solution C was added, by which silver was supplied from the silver benzotriazole to convert a part of silver benzotriazole into silver bromide.

The resulting powdery crystals were collected by filtration and they were added to a polymer solution prepared by dissolving 20 g of polyvinyl butyral in 200 ml of isopropyl alcohol, followed by dispersing for 30 minutes by a homogenizer.

To 10 g of the above described silver benzotriazole emulsion containing photographic silver bromide was added a solution prepared by dissolving 0.40 g of Dye Releasing Compound (1) having the following formula:

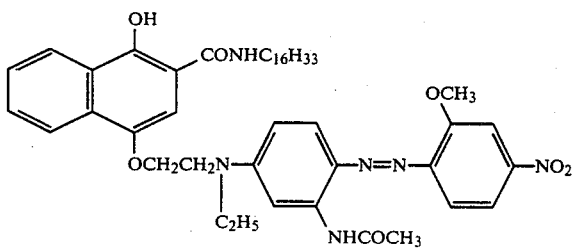

TABLE 1-continued

| Dye Releasing Compound | Amount Added (g) | Color Hue | Maximum Density |
|---|---|---|---|
| (7) | 0.35 | Yellow | 0.90 |

EXAMPLE 3

The same procedure as described in Example 1 was repeated except using the support as shown in Table 2 below in place of the support used in Example 1. The results thus obtained are shown in Table 2 below.

TABLE 2

| Support | Heat Treatment Temperature (°C.) | Time (min) | Maximum Density | Minimum Density |
|---|---|---|---|---|
| $+O-\bigcirc-\underset{CH_3}{\overset{CH_3}{C}}-\bigcirc-O\underset{O}{\overset{}{C}}\rightarrow_{90}-$ | 160 | 2 | 1.60 | 0.25 |
| $+O-\bigcirc-\underset{CH_3}{\overset{CH_3}{C}}-\bigcirc-OCH_2CH_2O-\underset{O}{\overset{}{C}}-\bigcirc-\underset{O}{\overset{}{C}}-OCH_2CH_2\rightarrow_{10}-$ | | | | |
| Cellulose Triacetate | 140 | 2 | 1.20 | 0.35 |
| Cellulost Diacetate | 140 | 2 | 1.25 | 0.45 |
| Polyester(bis-p-carboxyphenoxybutane and ethyleneglycol) | 160 | 2 | 1.70 | 0.25 |
| Polyamide(bis(30 aminopropyl)ether and heptamethylenediamine) | 140 | 2 | 1.50 | 0.20 |
| Polystyrene (MW: 10,000) | 160 | 2 | 0.60 | 0.05 |

0.18 g of 2,6-dichloro-p-aminophenol as a reducing agent and 0.22 g of guanidine trichloroacetate in a mixture of 4 ml of ethyl alcohol and 2 ml of N,N-dimethylformamide and stirred. The resulting mixture was applied to a polyethylene terephthalate film having a chickness of 180 μm at a wet film thickness of 100 μm. After the resulting photographic material was dried, it was imagewise exposed at 2,000 luxes for 10 seconds using a tungsten lamp. This imagewise exposed sample was uniformly heated for 60 seconds on a heat block heated at 180° C. After the sample was cooled to room temperature, the coated emulsion layer was mechanically peeled apart from the polyethylene terephthalate film using an adhesive tape. A clear magenta transferred negative image was obtained on the polyethylene terephthalate film. When the density of the magenta negative image was measured by a Macbeth transmission densitometer (TD-504), the maximum density to green light was 1.45 and the minimum density was 0.20. Further, the gradation of the sensitometric curve was a density difference of 0.75 to an exposure difference of 10 times in the straight line part.

EXAMPLE 2

The same procedure as described in Example 1 was repeated except using the dye releasing compound as shown in Table 1 below in place of Dye Releasing Compound (1) used in Example 1. The results thus obtained are shown in Table 1 below.

TABLE 1

| Dye Releasing Compound | Amount Added (g) | Color Hue | Maximum Density |
|---|---|---|---|
| (3) | 0.38 | Magenta | 1.65 |
| (4) | 0.41 | Cyan | 1.85 |
| (12) | 0.44 | Magenta | 1.15 |

EXAMPLE 4

A polyethylene terephthalate film having a white layer containing titanium dioxide on one surface thereof was used as a support. The procedure as described in Example 1 was repeated except coating the emulsion layer on the opposite surface of the support to the white layer. As a result of peeling apart the emulsion layer, a clear magenta reflective image was obtained in the polyethylene terephthalate film.

EXAMPLE 5

In place of the silver benzotriazole emulsion containing photographic silver bromide used in Example 1, a silver behenate emulsion containing photographic silver bromide was used.

The silver behenate emulsion containing photographic silver bromide was prepared in the following manner. 340 g of behenic acid was added to 500 ml of water and dissolved by heating to 85° C. with stirring. To the resulting solution, an aqueous solution containing 20 g of sodium hydroxide dissolved in 500 ml of water was added at a rate of 100 ml per minute.

The solution was cooled to 30° C., and a solution prepared by dissolving 85 g of silver nitrate in 500 ml of water was added to the above described solution at a rate of 100 ml per minute. The mixture was stirred at 30° C. for 90 minutes.

To the resulting solution, a solution prepared by dissolving 40 g of polyvinyl butyral in a mixture of 500 ml of butyl acetate and 500 ml of isopropyl alcohol was added, and the mixture was allowed to stand. Then, the liquid phase was removed, and the solid phase was subjected to centrifugal separation at 300 rpm for 30 minutes.

To the solid phase, 40 ml of isopropyl alcohol was added. The mixture was stirred for 10 minutes, and thereafter it was mixed with a solution prepared by dissolving 270 g of polyvinyl butyral in 800 ml of isopropyl alcohol, and the mixture was dispersed at 800 rpm for 30 minutes by a homogenizer. While maintaining the resulting solution at 50° C., 160 ml of an acetone solution containing 4.2% by weight of N-bromosuccinimide was added thereto and the mixture was reacted for 60 minutes, by which silver bromide was formed on a part of silver behenate.

A photographic material was prepared by the same procedure as described in Example 1, except that 10 g of the above described silver behenate emulsion containing photographic silver bromide, and the same operation as described in Example 1 was carried out. As a result, a transferred magenta negative image was obtained in the polyethylene terephthalate film. The magenta negative image has a maximum density of 1.0 as a transmission density to green light and a minimum density of 0.15.

EXAMPLE 6

The same procedure as described in Example 1 was repeated except further adding 0.5 g of o-phenylphenol as a diffusion accelerator. A transferred magenta image having the maximum density of 1.65 as a density to green light and the minimum density of 0.35 was obtained in the polyethylene terephthalate film.

EXAMPLE 7

6.5 g of benzotriazole and 10 g of gelatin were dissolved in 100 ml of water. The solution was stirred while maintaining at 50° C. and to which was added a solution containing 8.5 g of silver nitrate dissolved in 100 ml of water for 2 minutes. Then, a solution containing 1.2 g of potassium bromide dissolved in 50 ml of water was added to the above described solution for 2 minutes. The resulting emulsion was precipitated by controlling pH to remove an excess salt. The pH of the emulsion was adjusted to 6.0. The yield was 20.0 g.

A dispersion of a dye releasing compound in gelatin was prepared in the following manner. 15 g of Dye Releasing Compound (9) and 0.5 g of sodium 2-ethylhexylsulfosuccinate as a surface active agent were dissolved in 20 ml of ethyl acetate and 4 ml of N,N-dimethylformamide. The solution was mixed with 100 g of a 10% aqueous gelatin solution with stirring and dispersed at 10,000 rpm for 10 minutes using a homogenizer. The resulting dispersion was designated a dispersion of dye releasing compound.

A coating mixture was prepared in the following manner.

| (a) | Silver benzotriazole emulsion containing photographic silver bromide | 10 g |
| (b) | Dispersion of dye releasing compound | 3 g |
| (c) | 5% by weight methanol solution of guanidine trichloroacetate | 2 ml |

The above described components (a), (b) and (c) were mixed with stirring and coated on a polyethylene terephthalate film having a thickness of 180 μm at a wet film thickness of 100 μm. After drying, the resulting sample was imagewise exposed at 2,000 luxes for 10 seconds using a tungsten lamp. The sample was then uniformly heated on a heat block heated at 160° C. for 60 seconds. After the sample was cooled to room temperature, the emulsion layer was removed to obtain a transferred magenta negative image on the polyethylene terephthalate film. The transferred image had the maximum density of 0.88 and the minimum density of 0.15 to green light.

While the invention has been described in detail and with reference to specific embodiments thereof, it will be apparent to one skilled in the art that various changes and modifications can be made therein without departing from the spirit and scope thereof.

What is claimed is:

1. A heat-developable color photographic material comprising a support having thereon a layer containing at least a photographic silver halide and the photographic material containing an organic silver salt oxidizing agent, a reducing agent, a binder and a dye releasing compound which releases a diffusible dye upon heat development wherein the dye releasing compound is represented by the following general formula:

C—L—D where C represents a moiety capable of bonding to an oxidized product which is formed by a reaction between a reducing agent and an organic silver salt oxidizing agent; D represents a dye portion for forming an image which does not contain a carboxylic acid group or a sulfonic acid group; and L represents a connection group between C and D and the bond between C and L is cleaved upon the reaction of C with the oxidized product of the reducing agent; and the support is capable of receiving the released dye or the support has a layer composed of an organic high molecular weight compound which is capable of receiving the released dye.

2. A method of forming a color image which comprises (1) imagewise exposing a heat-developable color photographic material comprising a support having thereon a layer containing at least a photographic silver halide, the photographic material containing an organic silver salt oxidizing agent, a reducing agent, a binder and a dye releasing compound which releases a diffusible image forming dye upon heat development wherein the dye releasing compound is represented by the following general formula:

C—L—D where C represents a moiety capable of bonding to an oxidized product which is formed by a reaction between a reducing agent and an organic silver salt oxidizing agent; D represents a dye portion for forming an image which does not contain a carboxylic group or sulfonic acid group; and L represents a connection group between C and D and the bond between C and L is cleaved upon the reaction of C with the oxidized product of the reducing agent; and the support is capable of receiving a released dye or the support having thereon a layer compound of an organic high molecular weight compound which is capable of receiving a released dye, (2) developing the exposed photographic material by uniformly heating to release a diffusible dye and (3) diffusing the diffusible dye into the support or the layer capable of receiving the released dye.

3. A heat-developable color photographic material as claimed in claim 1, wherein the moiety represented by C includes an active methylene residue, an active methine residue, a phenol residue or a naphthol residue.

4. A heat-developable color photographic material as claimed in claim 3, wherein the moiety represented by C is represented by the following general formula (I), (II), (III), (IV), (V), (VI), or (VII):

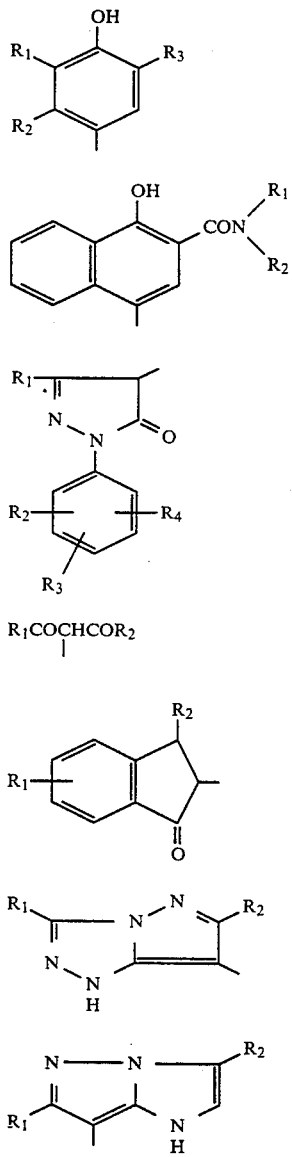

wherein $R_1$, $R_2$, $R_3$ and $R_4$ independently represent a hydrogen atom or a substituent selected from the group consisting of an alkyl group, a cycloalkyl group, an aryl group, an alkoxy group, an aryloxy group, an aralkyl group, an acyl group, an acylamino group, an alkoxyalkyl group, an aryloxyalkyl group, an N-substituted carbamoyl group, an alkylamino group, an arylamino group, a halogen atom, an acyloxy group, an acyloxyalkyl group and a cyano group, and these substituents may be further substituted with a hydroxyl group, a carboxyl group, a sulfo group, a cyano group, a nitro group, a sulfamoyl group, an N-substituted sulfamoyl group, a carbamoyl group, an N-substituted carbamoyl group, an acylamino group, an alkylsulfonylamino group, an arylsulfonylamino group, an alkyl group, an aryl group, an alkoxy group, an aryloxy group, an aralkyl group or an acyl group.

5. A heat-developable color photographic material as claimed in claim 1, wherein the moiety represented by C contains a ballast group.

6. A heat-developable color photographic material as claimed in claim 5, wherein the ballast group is a hydrophobic group selected from an alkyl group, an alkoxyalkyl group and an aryloxyalkyl group.

7. A heat-developable color photographic material as claimed in claim 5, wherein the ballast group is a hydrophilic group selected from a carboxy group or a salt thereof, a sulfo group or a salt thereof, a phosphoric acid group or a salt thereof, a carbonamido group and a sulfonamido group.

8. A heat-developable color photographic material as claimed in claim 1, wherein a total number of the carbon atoms contained in the moiety C is 12 or more.

9. A heat-developable color photographic material as claimed in claim 1, wherein the connecting group represented by L is a divalent group connecting between the moiety C and the dye portion D with a covalent bond.

10. A heat-developable color photographic material as claimed in claim 9, wherein the divalent group is selected from the group represented by the following general formulae:

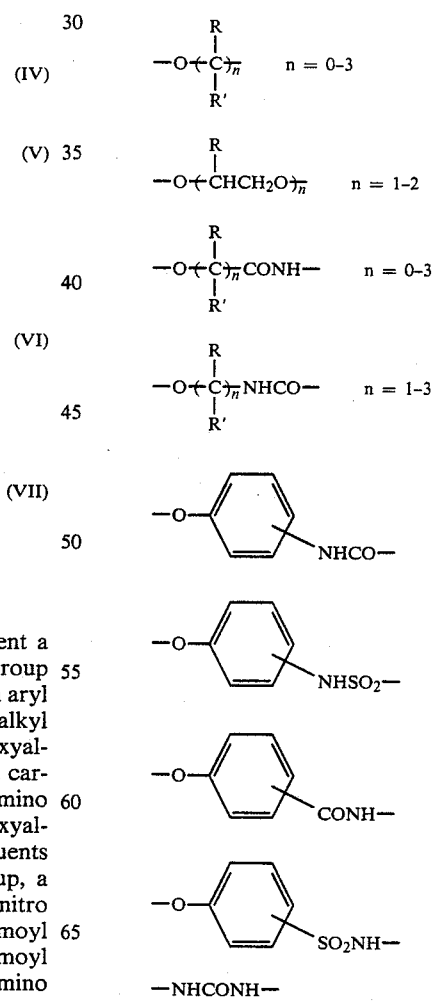

—NHCONH—

-continued

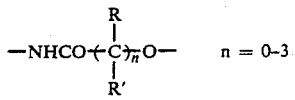 n = 0-3

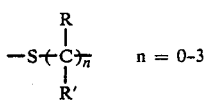 n = 0-3

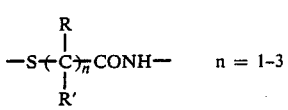 n = 1-3

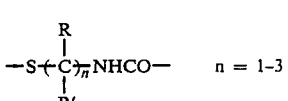 n = 1-3

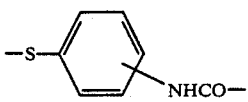

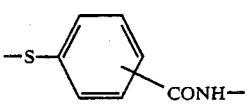

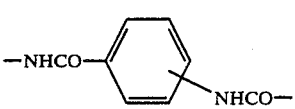

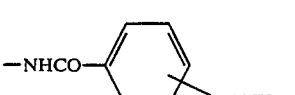

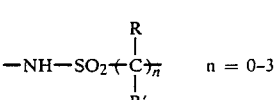 n = 0-3

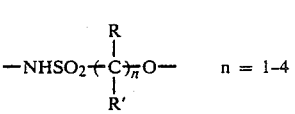 n = 1-4

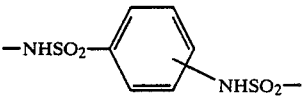

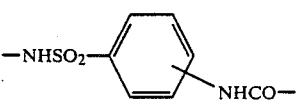

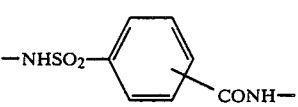

wherein R and R' independently represent a hydrogen atom, a methyl group or an ethyl group, and the benzene ring may further be substituted with an alkyl group, an alkoxy group or a halogen atom.

11. A heat-developable color photographic material as claimed in claim 9, wherein the divalent group is an O-releasing type group or an S-releasing type group and each group contains a total number of the carbon atoms of not more than 12.

12. A heat-developable color photographic material as claimed in claim 1, wherein the dye portion represented by D includes an azo dye, an azomethine dye, an anthraquinone dye, a naphthoquinone dye, a styryl dye, a quinophthalone dye or a phthalocyanine dye.

13. A heat-developable color photographic material as claimed in claim 12, wherein the dye included in the dye portion represented by D is represented by the following general formulae:

Yellow:

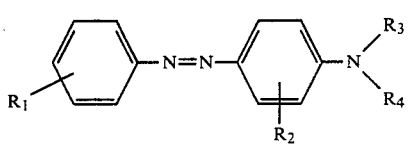

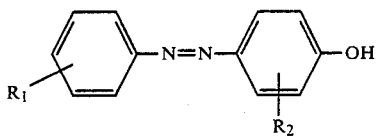

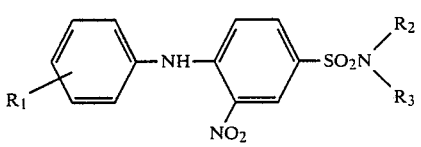

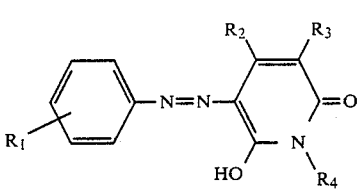

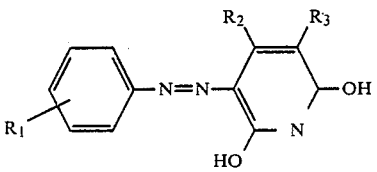

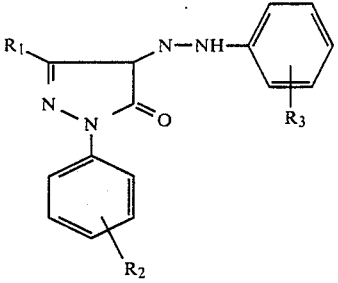

4,507,380
-continued
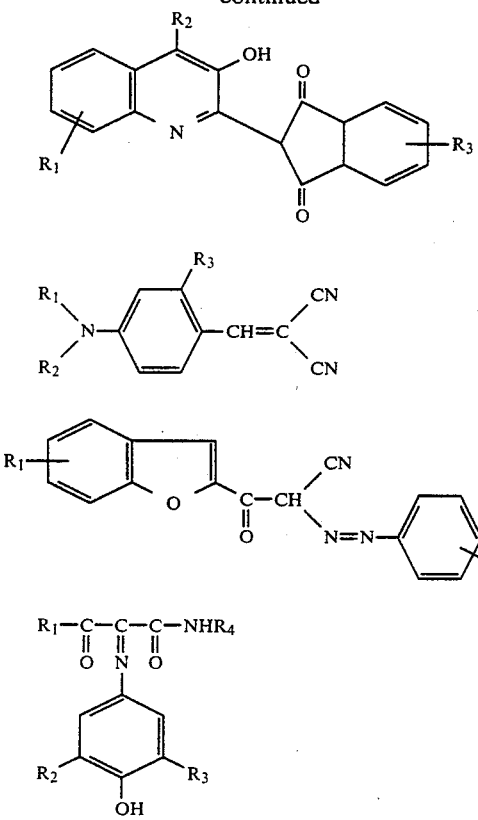
Magenta:
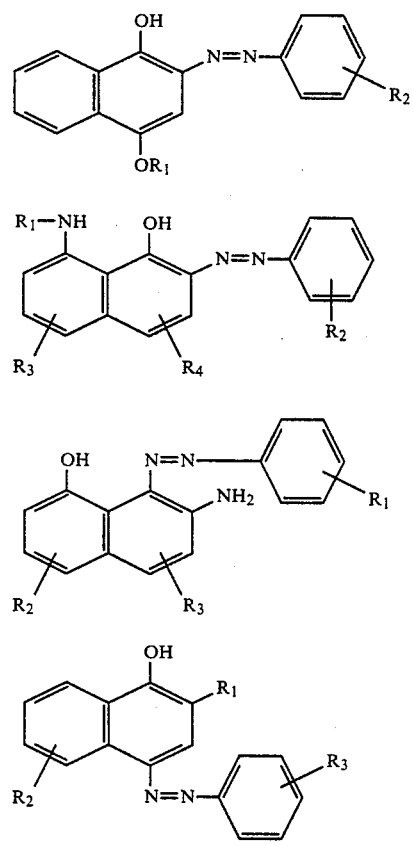
-continued
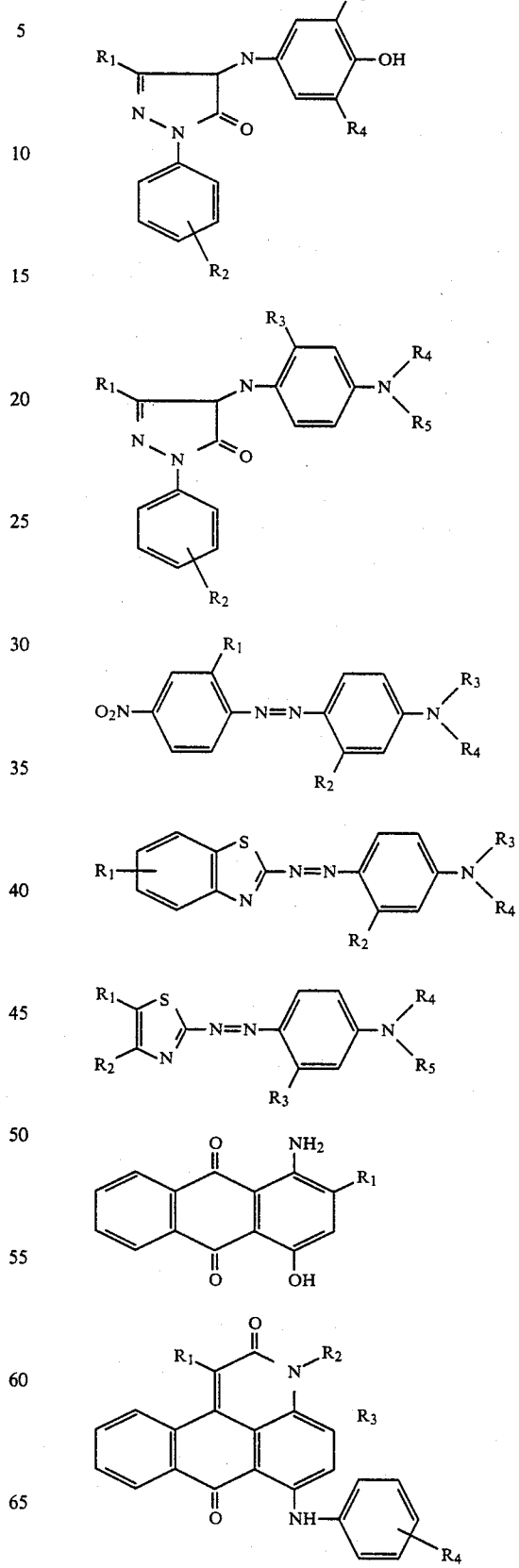

-continued
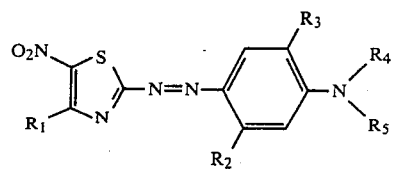
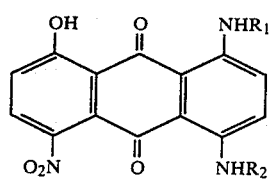
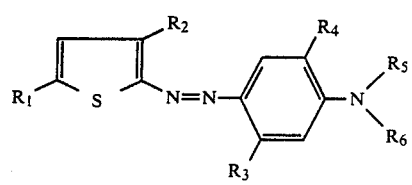
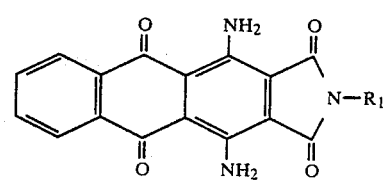
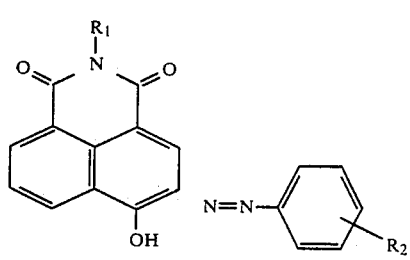
Cyan:
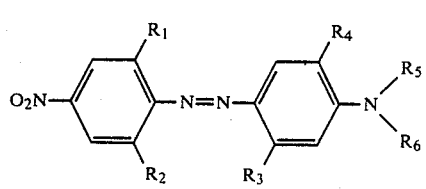
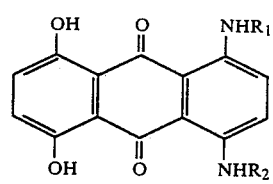
-continued
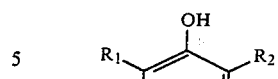
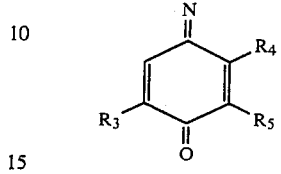
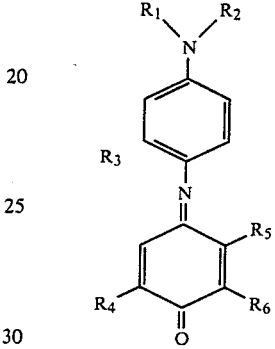
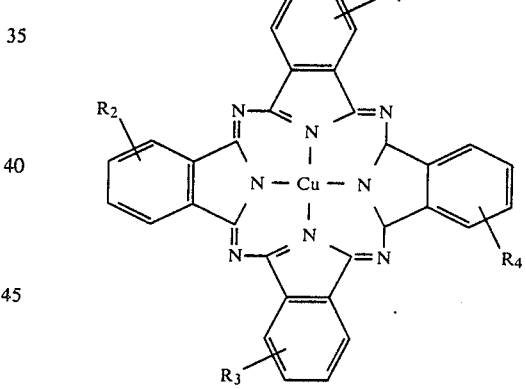
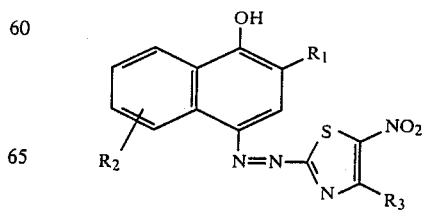
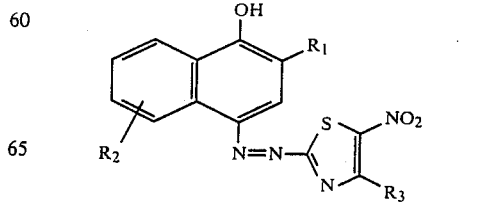

-continued

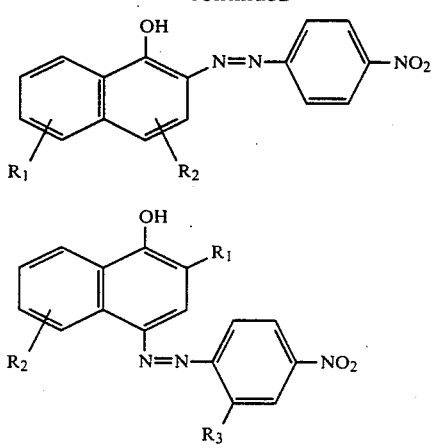

wherein $R_1$ to $R_6$ independently represent a hydrogen atom or a substituent selected from the group consisting of an alkyl group, a cycloalkyl group, an aralkyl group, an alkoxy group, an aryloxy group, an aryl group, an acylamino group, an acyl group, a cyano group, a hydroxy group, an alkylsulfonylamino group, an arylsulfonylamino group, an alkylsulfonyl group, a hydroxyalkyl group, a cyanoalkyl group, an alkoxycarbonylalkyl group, an alkoxyalkyl group, an aryloxyalkyl group, a nitro group, a halogen atom, a sulfamoyl group, an N-substituted sulfamoyl group, a carbamoyl group, an N-substituted carbamoyl group, an acyloxyalkyl group, an amino group, a substituted amino group, an alkylthio group and an arylthio group.

14. A heat-developable color photographic material as claimed in claim 1, wherein an amount of the dye releasing compound is from 0.01 mol to 4 mols per mol of the organic silver salt oxidizing agent.

15. A heat-developable color photographic material as claimed in claim 1, wherein the photographic silver halide is silver chloride, silver chlorobromide, silver chloroiodide, silver bromide, silver iodobromide, silver chloroiodobromide or silver iodide.

16. A heat-developable color photographic material as claimed in claim 1, wherein the photographic silver halide is present in a range from 0.005 mol to 5 mols per mol of the organic silver salt oxidizing agent.

17. A heat-developable color photographic material as claimed in claim 1, wherein the particle size of the silver halide is from 0.001 μm to 2 μm.

18. A heat-developable color photographic material as claimed in claim 1, wherein the organic silver salt oxidizing agent is a silver salt which forms silver by reacting with the reducing agent, when it is heated to a temperature of above 80° C. in the presence of exposed silver halide.

19. A heat-developable color photographic material as claimed in claim 1, wherein the organic silver salt oxidizing agent is a silver salt of an organic compound having a carboxy group, a silver salt of a compound containing a mercapto group or a thione group or a silver salt of a compound containing an imino group.

20. A heat-developable color photographic material as claimed in claim 1, wherein the photographic and the organic silver salt oxidizing agent are present in the same layer.

21. A heat-developable color photographic material as claimed in claim 1, wherein the binder is a hydrophilic colloid.

22. A heat-developable color photographic material as claimed in claim 1, wherein the binder is a hydrophobic polymer.

23. A heat-developable color photographic material as claimed in claim 1, wherein the hydrophobic polymer is polyvinyl butyral, polyvinyl acetate, ethyl cellulose, polymethyl methacrylate or cellulose acetate butyrate.

24. A heat-developable color photographic material as claimed in claim 1, wherein the support capable of receiving a released dye is composed of an organic high molecular weight compound having a glass transition temperature of from 40° C. to 250° C.

25. A heat-developable color photographic material as claimed in claim 1, wherein the organic high molecular weight compound in the layer has a glass transition temperature of from 40° C. to 250° C.

26. A heat-developable color photographic material as claimed in claim 1, wherein the reducing agent is a compound which is oxidized by the organic silver salt oxidizing agent to form an oxidized product capable of reacting with the dye releasing compound and releasing a dye.

27. A heat-developable color photographic material as claimed in claim 26, wherein the reducing agent is a color developing agent which is capable of forming an image upon oxidative coupling.

28. A heat-developable color photographic material as claimed in claim 27, wherein the color developing agent is a p-phenylenediamine type color developing agent, an aminophenol compound, an aminonaphthol compound, an aminohydroxypyrazole compound, an aminopyrazoline compound or a hydrazone compound.

29. A heat-developable color photographic material as claimed in claim 1, wherein the color photographic material further contains an auxiliary developing agent.

30. A heat-developable color photographic material as claimed in claim 1, wherein a color photographic material further contains a base or a base releasing agent.

31. A heat-developable color photographic material as claimed in claim 1, wherein the color photographic material further contains a diffusion accelerator.

32. A heat-developable color photographic material as claimed in claim 1, wherein the color photographic material further contains a thermal solvent.

33. A method of forming a color image as claimed in claim 2, wherein the heating is carried out at a temperature ranging from 80° C. to 250° C.

* * * * *